United States Patent [19]

Umezawa et al.

[11] 4,438,109
[45] Mar. 20, 1984

[54] TYLOSIN DERIVATIVES

[75] Inventors: Hamao Umezawa; Sumio Umezawa, both of Tokyo; Tsutomu Tsuchiya; Akihiro Tanaka, both of Kanagawa, all of Japan

[73] Assignee: Zaidan Hojin Biseibutsu Kanaku Kenkyu Kai, Tokyo, Japan

[21] Appl. No.: 285,747

[22] Filed: Jul. 22, 1981

[30] Foreign Application Priority Data

| Jul. 25, 1980 | [JP] | Japan | 55-101933 |
| Aug. 28, 1980 | [JP] | Japan | 55-118915 |
| Nov. 6, 1980 | [JP] | Japan | 55-156263 |
| Jan. 6, 1981 | [JP] | Japan | 56-573 |
| Jan. 6, 1981 | [JP] | Japan | 56-574 |
| Jan. 6, 1981 | [JP] | Japan | 56-575 |
| Feb. 25, 1981 | [JP] | Japan | 56-26457 |
| Jun. 19, 1981 | [JP] | Japan | 56-93782 |

[51] Int. Cl.³ .................. A61K 31/70; C07H 17/08
[52] U.S. Cl. .................... 424/180; 536/7.1
[58] Field of Search ........... 424/180; 536/17 R, 17 C, 536/11, 9, 115, 119, 122, 7.1

[56] References Cited

U.S. PATENT DOCUMENTS

| 3,480,613 | 11/1969 | Walton et al. | 536/119 |
| 3,574,187 | 4/1971 | Bannister | 536/11 |
| 3,681,321 | 8/1972 | Magerlein | 536/11 |
| 4,017,607 | 4/1977 | Inouye et al. | 536/9 |
| 4,036,853 | 7/1977 | Sciavolino | 536/9 |
| 4,078,139 | 3/1978 | Barton et al. | 536/115 |
| 4,156,078 | 5/1979 | Umezawa et al. | 536/17 R |
| 4,178,436 | 12/1979 | Sciavolino | 536/9 |
| 4,273,923 | 6/1981 | Igarashi et al. | 536/17 R |
| 4,307,085 | 12/1981 | Waitz et al. | 536/17 R |
| 4,324,888 | 4/1982 | Rathborn | 536/122 |

OTHER PUBLICATIONS

Tanaka, et al., "Bull. Chem. Soc. Japan", vol. 54, 1981, pp. 3837-3845.
Tanaka et al., "Jour. of Antibiotics", vol. 34, 1981, pp. 1374-1376, 1377-1380.
Omura, "Durwent Abstracts", 82541D/45 of Japanese Kokai J56122-397, 9/1981.

Primary Examiner—Johnnie R. Brown
Attorney, Agent, or Firm—Burgess, Ryan & Wayne

[57] ABSTRACT

Tylosin derivatives shown by the general formula

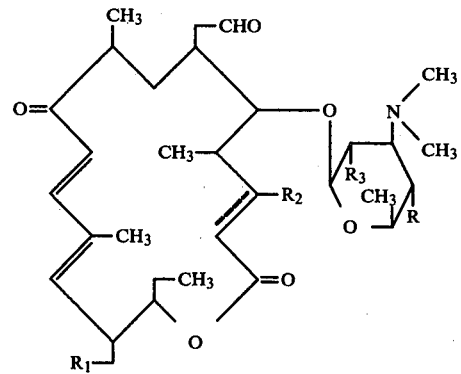

wherein R represents a hydrogen atom or a hydroxyl group; $R_1$ represents a halogen atom, a hydroxyl group, a tetrahydrofuranyloxy group, a tetrahydropyranyloxy group, a tetrahydrothiofuranyloxy group, a tetrahydrothiopyranyloxy group, an alkanoyloxy group, an arylcarbonyloxy group, an aralkylcarbonyloxy group, a lower alkylthiomethyloxy group, a heterocyclic thio group which may have a substituent, a mono- or di-lower alkylamino lower alkylthio group or a group of

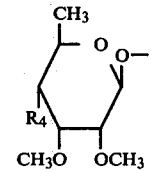

(wherein $R_4$ represents a hydroxyl group or an alkanoyloxy group); $R_2$ represents a hydrogen atom, a hydroxyl group, or an alkanoyloxy group; $R_3$ represents a hydroxyl group or an alkanoyloxy group; and ===== represents a single bond or a double bond, but represents a double bond when $R_2$ is a hydrogen atom.

These compounds are useful as antibiotics.

15 Claims, No Drawings

TYLOSIN DERIVATIVES

DETAILED DESCRIPTION OF THE INVENTION

This invention relates to tylosin derivatives. Tylosin itself is a useful compound which is commercially available as macrolide antibiotics. The tylosin derivatives of this invention are shown by the following general formula and are very useful antibiotics having greater antibiotic activity than tylosin;

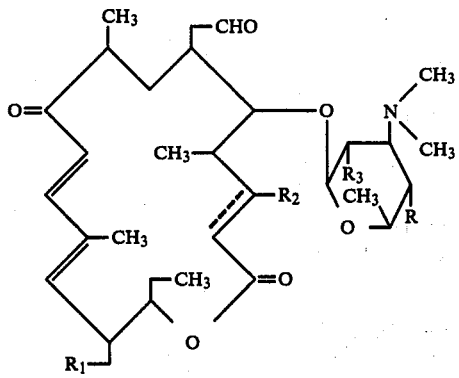

wherein R represents a hydrogen atom or a hydroxyl group; $R_1$ represents a halogen atom, a hydroxyl group, a tetrahydrofuranyloxy group, a tetrahydropyranyloxy group, a tetrahydrothiofuranyloxy group, a tetrahydrothiopyranyloxy group, an alkanoyloxy group, an arylcarbonyloxy group, an aralkylcarbonyloxy group, a lower alkylthiomethyloxy group, a heterocyclic thio group which may have a substituent, a mono- or di-lower alkylamino lower alkylthio group or a group shown by the formula

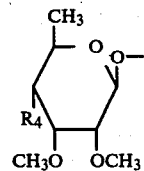

(wherein $R_4$ represents a hydroxyl group or an alkanoyloxy group); $R_2$ represents a hydrogen atom, a hydroxyl group, or an alkanoyloxy group; $R_3$ represents a hydroxyl group or an alkanoyloxy group; and ==== represents a single bond or a double bond but represents a double bond when $R_2$ is a hydrogen atom.

In the above compounds of formula I, examples of the alkanoyloxy group are an acetyloxy group, propionyloxy group, butyryloxy group, isobutyryloxy group, valeryloxy group, isovaleryloxy group, etc.; examples of the arylcarbonyloxy group are benzoyloxy group, naphthoyloxy group, etc.; and examples of the aralkylcarbonyloxy group are benzylcarbonyloxy group, phenethylcarbonyloxy group, etc. Also, examples of the lower alkylthiomethyloxy group are methylthiomethyloxy group, ethylthiomethyloxy group, isopropylthiomethyloxy group, butylthiomethyloxy group, etc., and examples of the heterocyclic thio group are thienylthio group, pyrrolylthio group, pyrrolidinylthio group, pyridylthio group, piperidinylthio group, pyrazinylthio group, thiazolylthio group, thiadiazolylthio group, triazolylthio group, tetrazolylthio group, morpholinothio group, etc. These heterocyclic groups may have a substituent such as, for example, a lower alkyl group (e.g., methyl group, ethyl group, isopropyl group, butyl group, etc.), a lower alkoxy group (e.g., methoxy group, ethoxy group, propoxy group, etc.,). Also, examples of the mono- or di-lower alkylamino lower alkylthio group are methylaminomethylthio group, ethylaminoethylthio group, dimethylaminoethylthio group, diethylaminopropylthio group, etc.

The tylosin derivatives of this invention shown by general formula I can be produced in the following manner.

Process 1:

In the tylosin derivatives of this invention shown by the general formula I, the compound shown by the following general formula

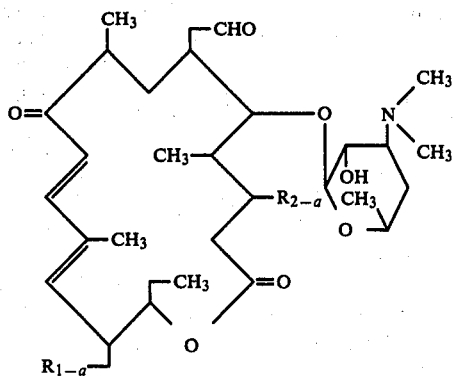

wherein $R_{1-a}$ represents a hydroxyl group, an alkanoyloxy group or a group shown by the formula

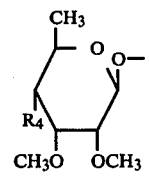

(wherein $R_4$ has the same significance as defined above and $R_{2-a}$ represents a hydroxyl group or an alkanoyloxy group, can be obtained by reacting the compound shown by the general formula

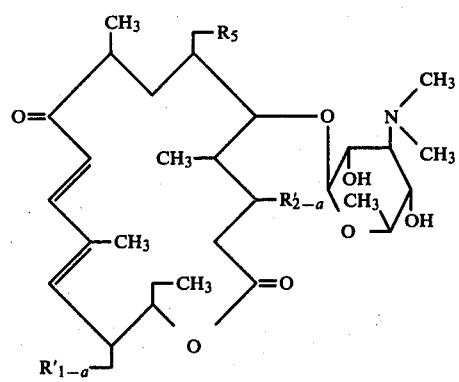

wherein $R_{1-a}'$ represents an alkanoyloxy group, a hydroxyl group having a protective group or a group shown by

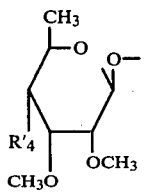

(wherein $R_4'$ represents an alkanoyloxy group or a hydroxyl group having a protective group); $R_{2-a}'$ represents a hydroxyl group, an alkanoyloxy group, or a hydroxyl group having a protective group; and $R_5$ represents a protected aldehyde group, with a (substituted) benzylsulfonic acid or a reactive derivative thereof to form a 4'-position sulfonic acid ester product (step 1), reacting the product with an alkali metal halide to form a 4'-position halogen-substituted product (step 2), reacting the product with a tri-substituted tin hydride to effect the dehalogenation to form a 4'-position deoxy product (step 3), and removing the protective group for the aldehyde group of the product obtained, and, further, when $R_{1-a}'$ (or $R_4'$) and/or $R_{2-a}'$ is a hydroxyl group having a protective group, removing the protective group(s) simultaneously or successively (step 4). The reaction is shown by the following reaction formula:

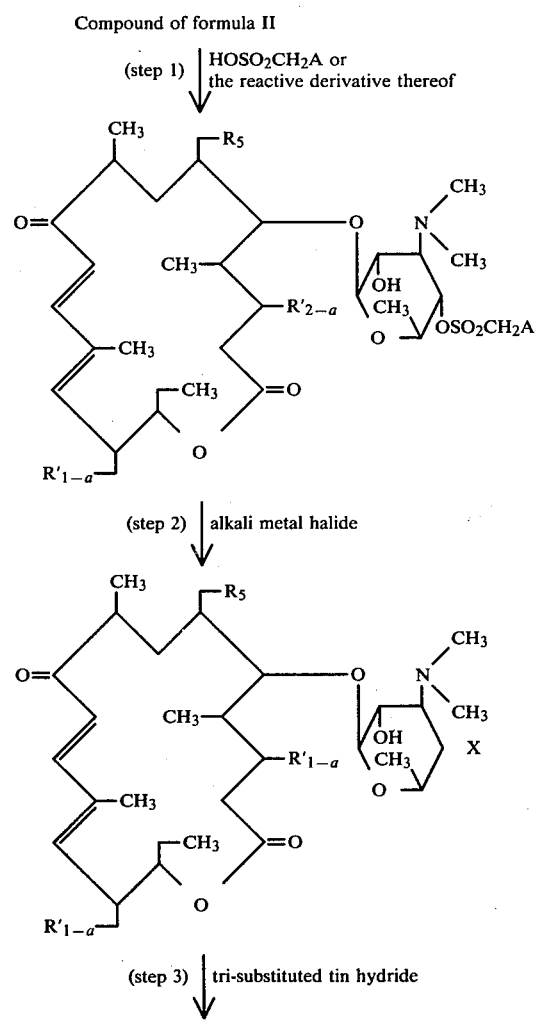

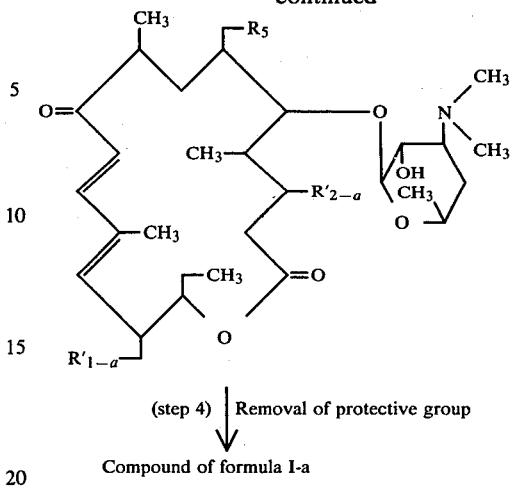

(step 4) | Removal of protective group

Compound of formula I-a

In the formulae described above, A represents a phenyl group which may have been substituted by a lower alkyl group having 1-3 carbon atoms and X represents a halogen atom.

The protected aldehyde group shown by $R_5$ in the raw material of formula II is an aldehyde group protected as a form of acetal or thioacetal and practical examples thereof are dimethylacetal, diethylacetal, diethylthioacetal, ethyleneacetal, ethylenethioacetal, propyleneacetal, which may have a substituent such as methyl group. Also, as the protective group for the hydroxyl group shown by $R_{1-a}'$, $R_{2-a}'$ and $R_4'$, there are substituted alkoxymethyl groups such as methoxymethyl group, ethoxymethyl group, methoxyethoxymethyl group, etc., as well as furan-2-yl group, pyran-2-yl group, etc.

Each of the aforesaid steps are explained below.

Step 1:

In this step the compound of formula II is reacted with benzylsulfonic acid or a reactive derivative thereof.

Benzylsulfonic acid used in the reaction may have 1-3 substituents such as methyl group, ethyl group, etc., at the benzene ring. Also, as the reactive derivative of benzylsulfonic acid, the halide such as chloride, bromide, etc., or the acid anhydride of benzylsulfonic acid is used. The reaction is usually performed at room temperature or under cooling in a solvent. As the solvent, there are nonprotonic solvents such as acetonitrile, acetone, dimethyl sulfoxide, dioxane, etc. In this reaction, it is preferred to use a basic catalyst such as pyridine, triethylamine, etc., in particular, pyridine.

Step 2:

In this step the benzylsulfonic acid ester at the 4'-position of the product is replaced with a halogen atom. For the halogen substitution, an alkali metal halide, in particular sodium iodide (NaI), lithium chloride, lithium bromide, etc., is used. The reaction is usually performed at room temperature or under heating using the above-described nonprotonic solvent. Heating may be performed at about the boiling point of the solvent used or may be performed in a closed tube at a temperature higher than the boiling point.

Step 3:

In this step the halogen atom at the 4'-position of the product is replaced with hydrogen atom, which is performed by reacting the compound of formula IV with a reducing agent, in particular tri-substituted tin halide. Examples of the tri-substituted tin halide are a trialkyltin halide such as triethyltin halide, tri-n-butyltin halide, etc., and a triaryltin halide such as triphenyltin halide. A suitable reaction solvent is a nonprotonic solvent which does not contain halogen atom and is reluctant to be reduced, such as toluene, benzene, dioxane, tetrahydrofuran, etc. The reaction proceeds at room temperature or under heating but for promoting the reaction, it is preferred to add a radical initiator such as α,α-azobisisobutyronitrile (AIBN), etc.

Step 4:

In this step the protective group for the aldehyde group of the 4'-position deoxy product of formula V is removed and further when $R_{1-a}'$ (or $R_4'$) and/or $R_{2-a}'$ is a hydroxyl group having a protective group, said protective group(s) is also removed. The removal of the protective group for the aldehyde group is performed by treating the product of formula V with a mineral acid such as hydrochloric acid, sulfuric acid, etc., or an organic acid such as trifluoroacetic acid, trichloroacetic acid, etc., usually in the presence of water. Also, the removal of the protective group for the hydroxyl group may be performed using an arylsulfonic acid such as p-toluenesulfonic acid, etc., an alkylsulfonic acid such as methanesulfonic acid, etc., or the aforesaid acid used for the removal of the aldehyde group. This reaction is performed in a solvent at room temperature or under heating and as the solvent, an acid-stable nonprotonic solvent such as dioxane, dimethylformamide, dimethyl sulfoxide, etc, may be used.

Process 2:

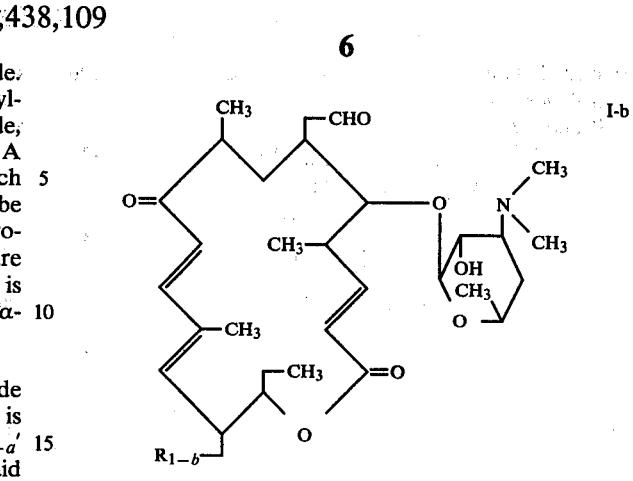

wherein $R_{1-b}$ represents a hydroxyl group or

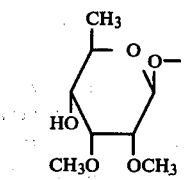

can be obtained by treating the compound of formula V (wherein, however, $R_{2-a}'$ is an alkanoyloxy group), which is an intermediate product in process 1; with a base and then removing the protective group for the aldehyde group. The reaction is shown by the following reaction formula:

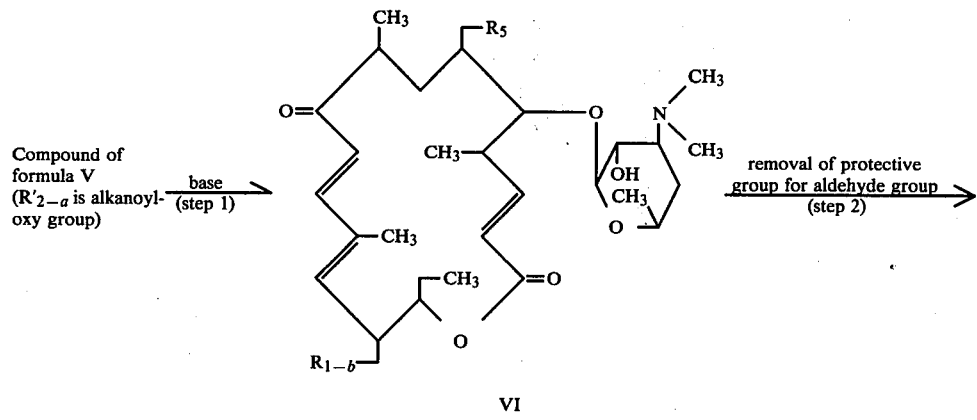

Compound of formula I-b

Each step of the process is explained below:

Step 1:

In this step the treatment by a base is performed at room temperature or by heating. When a solvent is used in the reaction, water, alcohol, dioxane, tetrahydrofuran, etc., is properly used. As the base used in this step, there are aqueous ammonia; primary, secondary, and tertiary amines such as methylamine, ethylamine, dimethylamine, trimethylamine, etc.; diazabicycloic amines, potassium t-butoxide; and inorganic bases such as potassium hydroxide, sodium hydroxide, sodium carbonate, potassium carbonate, etc.

Step 2:

In the tylosin derivatives shown by formula I, the compound shown by the general formula Then, the protective group of the aldehyde group of the 3,4'-dideoxy product of formula VI thus obtained is removed. This can be performed by the process of step 4 in Process 1.

Process 3:

In the tylosin derivatives of formula I, the compound shown by the general formula

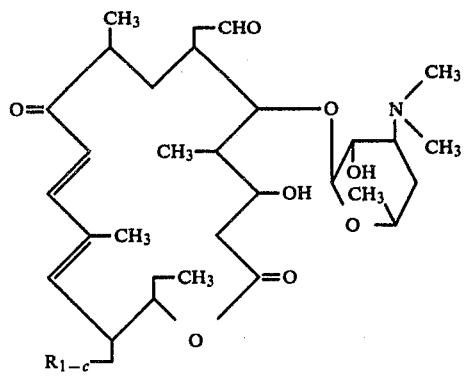

I-c wherein $R_{1-c}$ represents a tetrahydrofuranyloxy group, a tetrahydropyranyloxy group, a tetrahydrothiofuranyloxy group, a tetrahydrothiopyranyloxy group, an alkanoyloxy group, an arylcarbonyloxy group, an aralkylcarbonyloxy group, or a lower alkylthiomethyloxy group, can be obtained by (1) reacting the compound shown by the general formula

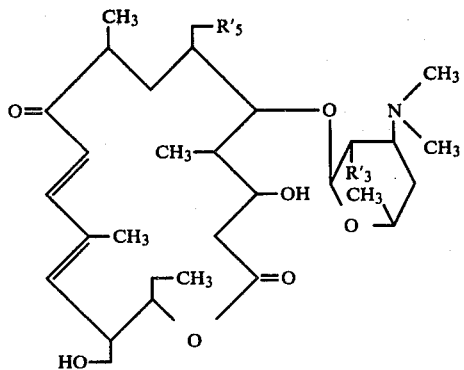

VII wherein $R_5'$ represents an aldehyde group which may have a protective group and $R_3'$ represents an alkanoyloxy group, with (a) the carboxylic acid halide shown by the general formula $$R_6-CO-X \qquad \text{VIII}$$

wherein $R_6$ represents a lower alkyl group, an aryl group, or an aralkyl group and X represents a halogen atom, (b) the compound shown by the general formula $$R_{1-c}'-CO-R_7 \qquad \text{IX}$$

wherein $R_{1-c}'$ represents a tetrahydrothiofuranyloxy group or a tetrahydrothiopyranyloxy group and $R_7$ represents a phenyl group, a diphenylacetyl group or an aralkyl group, (c) the methylsulfoxide compound shown by the general formula $$R_8-\underset{\underset{O}{\|}}{S}-CH_3 \qquad \text{X}$$

wherein $R_8$ represents a lower alkyl group, or (d) dihydrofuran or dihydropyran;

(2) then, hydrolyzing the product;

(3) and, further, when $R_5'$ is an aldehyde group having a protective group, removing the protective group.

The reaction is shown by the following reaction formula:

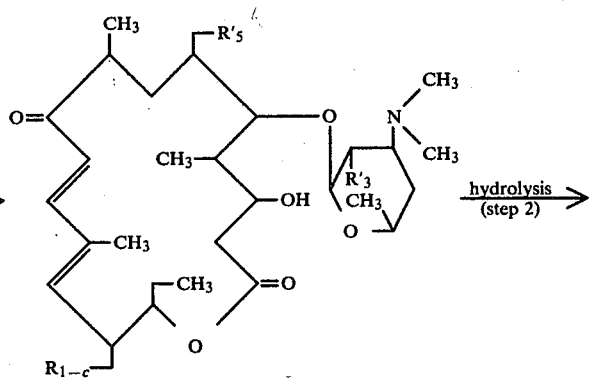

XI

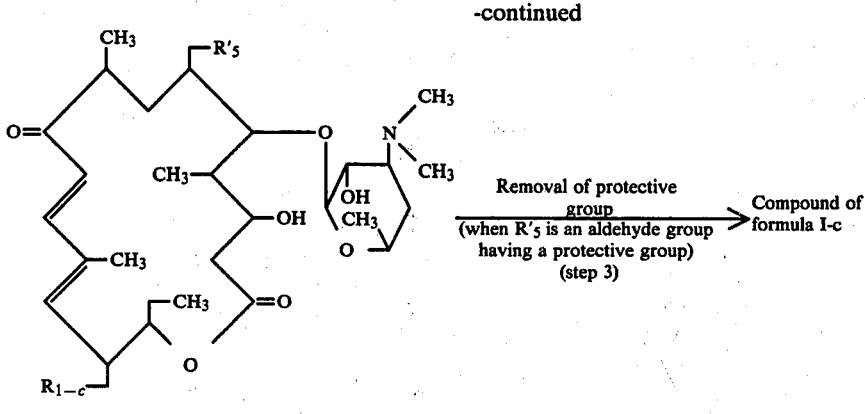

Each step is explained below:

Step 1:

(a). The reaction of the compound of formula VII and the compound of formula VIII can be performed in a basic solvent such as pyridine, triethylamine, etc.

(b). The reaction of the compound of formula VII and the compound of formula IX can be performed in an organic solvent such as methylene chloride, chloroform, carbon tetrachloride, tetrahydrofuran, acetonitrile, dioxane, dimethylformamide, dimethyl sulfoxide, etc., in the presence of an organic strong acid such as methanesulfonic acid, p-toluenesulfonic acid (p-TsOH), difluoroacetic acid, dichloroacetic acid, trifluoroacetic acid, trichloroacetic acid, etc., or a mineral acid such as sulfuric acid, hydrochloric acid, etc.

(c). The reaction of the compound of formula VII and the compound of formula X can be performed in the presence of acetic acid or acetic anhydride at room temperature or under heating in non-solvent or, when the compound of formula X is a solid material, in an organic solvent such as acetonitrile, tetrahydrofuran, dioxane, etc.

(d). The reaction of the compound of formula VII and dihydrofuran or dihydropyran is performed in a non-protonic solvent in the presence of a salt of a strong acid and a weak base. As the salt of a strong acid and a weak base, the salt of an organic acid and an organic base, such as pyridinium p-toluene sulfonate (PPTS) is effectively used. Dihydrofuran or dihydropyran used in the reaction may have a hydroxyl group, a lower alkyl group, a lower alkoxy group as a substituent. Also, as the non-protonic solvent, methylene chloride, acetonitrile, acetone, dimethylsulfoxide, dimethylformamide, etc., can be used. It is preferred that these solvents are anhydrous.

Step 2:

The hydrolysis can be performed in an ordinary way, e.g., under heating in an alcohol such as methanol, ethanol, etc.

Step 3:

The removal of the protective group for the aldehyde group can be performed by the same manner as in step 4 in Process 1.

Process 4:

In the tylosin derivatives of formula I, the compound shown by the general formula

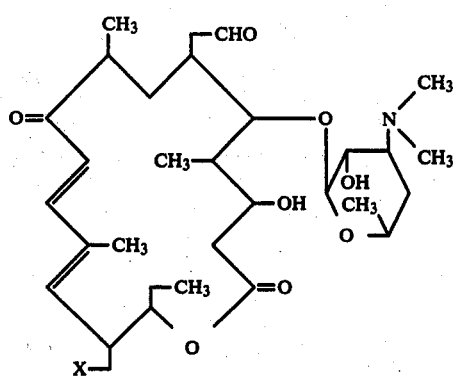

wherein X has the same significance as defined above, can be obtained by reacting the compound shown by the general formula

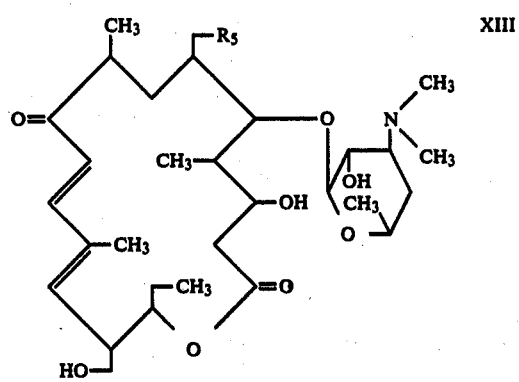

wherein $R_5$ has the same significance as defined above, with a halogenating agent and then removing the protective group for the aldehyde group.

The halogenation in the process is performed using a halogen atom such as chlorine, bromine, iodine, etc., or carbon tetrachloride, carbon tetrabromide, carbon iodide, etc. It is preferred for promoting the reaction to add triphenyl phosphine or, if necessary, a base such as pyridine. Among these additives, some additives may also act as solvent but if necessary, at least one solvent such as pyridine, acetonitrile, tetrahydrofuran, dioxane, etc., may be properly used. The removal of the protective group for the aldehyde group can be performed by the same manner as in step 4 in Process 1.

Process 5:

In the tylosin derivatives of formula I, the compound shown by the general formula

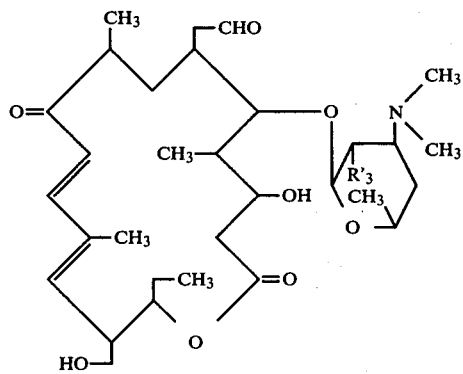

wherein $R_3'$ has the same meaning as defined above, can be obtained by reacting 4'-deoxymycaminosyl tylonolide shown by the formula

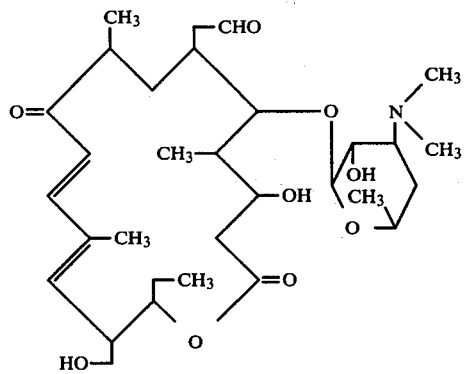

with the carboxylic acid shown by the general formula $$R_9\text{—COOH} \qquad \text{XIV}$$

wherein $R_9$ represents a lower alkyl group, or the reactive derivative thereof.

As the reactive derivatives of the carboxylic acid, there are acid halides, acid anhydrides, etc.

The reaction is performed in a solvent at room temperature or under cooling. As the solvent, a non-protonic solvent such as acetonitrile, acetone, dimethyl sulfoxide, dioxane, etc., is suitably used.

Process 6:

In the tylosin derivatives of formula I, the compound shown by the general formula

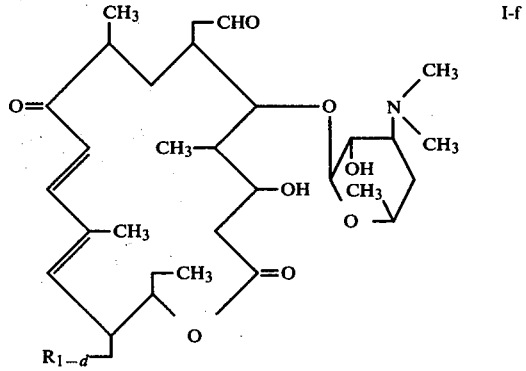

wherein $R_{1-d}$ represents a heterocyclic thio group which may have a substituent or a mono- or di-lower alkylamino lower alkylthio group, can be obtained by reacting the compound shown by the general formula

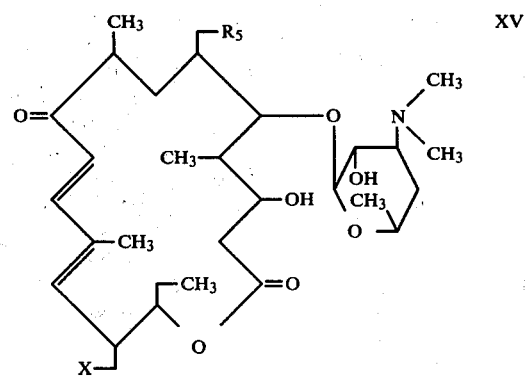

wherein X and $R_5$ have the same significance as defined above, with the compound shown by the general formula $$R_{1-d'}\text{—SH} \qquad \text{XVI}$$

wherein $R_{1-d'}$ represents a heterocyclic group which may have a substituent or a mono- or di-lower alkylamino lower alkyl group, and then removing the protective group for the aldehyde group.

The reaction of the compound of formula XV and the compound of formula XVI can be performed in an organic solvent such as methylene chloride, chloroform, carbon tetrachloride, tetrahydrofuran, acetonitrile, anhydrous acetonitrile, dioxane, dimethylformamide, dimethyl sulfoxide, etc., in the presence of an alkali metal hydride such as sodium hydride, etc.

The removal of the protective group for the aldehyde group from the product thus obtained can be performed by the same manner as in step 4 of Process 1.

Regarding the antimicrobial activity of the tylosin derivatives of this invention shown by formula I, the minimum inhibition concentration (MIC) is shown in Table I.

| Microorganism | MIC (γ/ml) Example No. | | | | | | | | |
|---|---|---|---|---|---|---|---|---|---|
| | 2 | 9 | 10 | 18 | 19 | 20 | 21 | 27 | Tylosin |
| Staph. aureus 209 P | 0.2 | 0.2 | 0.2 | <0.2 | <0.2 | <0.2 | 0.78 | <0.2 | 0.39 |
| Ataph. aureus MS 9861 | 3.12 | 1.56 | 3.12 | 0.2 | <0.2 | 3.12 | 6.25 | 0.78 | 6.25 |
| Staph. aureus MS 10225 | 3.12 | 0.78 | 0.2 | 0.2 | <0.2 | 0.78 | 6.25 | 0.39 | 3.12 |
| B. subtilis NRRL B-558 | 0.78 | 0.39 | <0.2 | <0.2 | <0.2 | <0.2 | 0.2 | <0.2 | 0.78 |
| E. coli NIHJ | 3.12 | 6.25 | 6.25 | 6.25 | 25 | 6.25 | 6.25 | 12.5 | 100 |
| Kleb. pneumoniae PCI 602 | 0.78 | 6.25 | 1.56 | 1.56 | 3.12 | 1.56 | 1.56 | 1.56 | 25 |
| Sh. dysenteriae JS 11910 | <0.2 | 0.78 | 0.2 | 0.39 | 0.39 | 0.78 | 0.39 | 0.2 | 12.5 |
| Sal. enteritidis 1891 | 0.78 | 1.56 | 0.78 | 1.56 | 1.56 | 0.78 | 0.39 | 0.78 | 25 |

The tylosin derivatives of this invention can be orally or parenterally administered as tablets, capsules, powders, injections, liquids, etc., prepared using ordinary carriers for preparation. The doses of the medicaments are 10–1000 mg per single dose and 1–4 times a day.

The invention will be explained in detail by the following examples.

In the physiochemical properties in Examples, NMR stands for a nuclear magentic resonance spectrum, IR an infrared absorption spectrum, m. p. a melting point, Anal. an elemental analysis value, and UV a ultraviolet absorption spectrum.

EXAMPLE 1

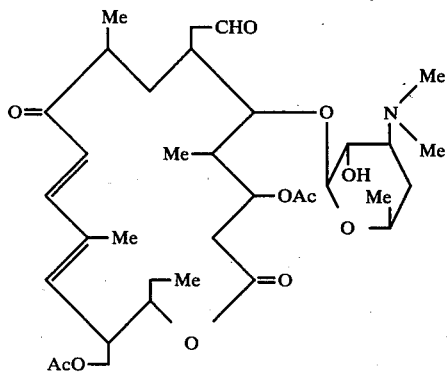

Ac: acetyl group and Me: methyl group.

(a). In 7.8 ml of anhydrous pyridine was dissolved in 392 mg of 3,23-di-O-acetylmycaminosyl tylonolide diethyl acetal and after adding thereto slowly 149 mg of benzylsulfonyl chloride at −40° C. (over a period of about 5 minutes), the reaction was performed for 2 hours. Then, 0.03 ml of water was added to the reaction mixture at −40° C. and the mixture was allowed to stand for 30 minutes at room temperature.

The reaction mixture was concentrated under reduced pressure, and after azeotropically distilling off pyridine with toluene, the residue was dissolved in 20 ml of chloroform, washed once each with 7 ml of a saturated aqueous sodium hydrogencarbonate solution, 7 ml of a saturated aqueous sodium chloride solution, and 7 ml of pure water, dried by anhydrous sodium sulfate, and concentrated under reduced pressure to provide 3,23-di-O-acetyl-4'-benzylsulfonyl mycaminoyl tylonolide diethyl acetal.

Since the product was unstable, the product was used in the subsequent reaction as it was. The amount of the product was 403 mg (yield of about 80%).

(b). In 8.1 ml of anhydrous methyl ethyl ketone was dissolved 403 mg of the product (containing impurities) obtained in step (a) described above and after adding thereto 99.8 mg of sodium iodide followed by closely sealing the reaction vessel, they were reacted for 20 minutes at 80° C. After the reaction was over, the solids precipitated were removed by filtration using a glass filter (G3) and the filtrate was washed several times with acetone, and concentrated under reduced pressure. When 16 ml of chloroform was added to the residue, precipitates formed again, which were recovered by filtration by means of a glass filter (G3) and washed several times with chloroform.

The chloroform solutions were combined and washed once each with 7 ml of a saturated aqueous sodium hydrogencarbonate solution, 7 ml of an aqueous 0.1 M sodium thiosulfate solution, and 7 ml of pure water, dried by anhydrous sodium sulfate, and concentrated under reduced pressure.

The residue thus obtained was subjected to chromatography by a column of 20 g silica gel (Kiesel gel-60, 230–400 mesh) and a cyclohexane-acetone (4:1) solvent system to provide 368 mg of 3,23-di-O-acetyl-4'-deoxy-4'-iodo mycaminosyl tylonolide diethyl acetal.

(c). In 6.3 ml of anhydrous benzene was dissolved 339 mg of the product obtained in aforesaid step (b) and after adding thereto 338 mg of tri-n-butyltin hydride and 6.3 mg of α,α'-azobisisobutyronitrile as a reaction initiator, the reaction vessel was closely sealed under a nitrogen stream and then the reaction was performed for 2 hours at 80° C.

Then, the reaction mixture obtained was concentrated under reduced pressure and the residue obtained was applied to a silica gel column followed by developing first with cyclohexaneacetone (4:1) solvent system and then with a chloroform-methanol (15:1) solvent system to provide 202 mg of 3,23-di-O-acetyl-4'-deoxy mycaminosyl tylonolide diethyl acetal(yield of 71%).

(d). In 1.4 ml of acetonitrile was dissolved 71.9 mg of the product obtained in aforesaid step (c) and after adding thereto 2.0 ml of 0.1 N hydrochloric acid, the reaction was performed for one hour at room temperature. Then, after adding water containing 25 mg of powdery sodium hydrogencarbonate to the reaction mixture, the product was extracted with chloroform.

The product obtained was subjected to chromatography using a silica gel colum and a chloroform-methanol (12:1) solvent system to provide 63.5 mg (yield of 98%) of 3,23-di-O-acetyl-4'-deoxy mycaminosyl tylonolide.

The product showed the following physicochemical properties:

| (i) NMR (CDCl$_3$) | | | |
|---|---|---|---|
| δ (ppm) | H no. | Form | J |
| 2.06 | 3 | s | 23-O—Ac |
| 2.13 | 3 | s | 3-O—Ac |
| 2.30 | 6 | s | —N(CH$_3$)$_2$ |
| 9.73 | 1 | like S | ⌐CHO |

(ii) Colorless amorphous solid (purified by acetone and n-hexane).
(iii) Anal. (for C$_{35}$H$_{55}$NO$_{11}$):

| | C (%) | H (%) | N (%) |
|---|---|---|---|
| Calculated | 63.14 | 8.33 | 2.10 |
| Found | 62.89 | 8.20 | 2.08 |

(iv) $[\alpha]_D^{24}$: +22° (c 1.0, CHCl$_3$)

(v) UV $\lambda_{max}^{MeOH}$: 280 nm (ε = 26,000)

(vi) Rf 0.30 Wakogel B-5 (trade name) chloroform-methanol (10:1)

In addition, 3,23-O-acetyl mycaminosyl tylonolide diethyl acetal used in step (a) of Example 1 was prepared by the process shown in following Reference example 1.

REFERENCE EXAMPLE 1

(a). In 8.3 ml of absolute ethanol was dissolved 825 mg of mycaminosyl tylonolide and after adding thereto 356 mg of anhydrous p-toluenesulfonic acid, the reaction was performed for 20 minutes at room temperature. Then, after adding 0.3 ml of triethylamine to the reaction mixture, the mixture was concentrated under reduced pressure. The residue was dissolved in chloroform, the solution was washed once each with a saturated aqueous sodium hydrogencarbonate solution, a saturated aqueous sodium chloride solution, and water, dried by anhydrous sodium sulfate, and concentrated under reduced pressure. The residue was subjected to chromatography using a silica gel columm and a chloroform-methanol (7:1) solvent system to provide 852 mg (yield of 92%) of mycaminosyl tylonolide diethyl acetal.

(b). In 10 ml of anhydrous pyridine was dissolved 992 mg of the product obtained in aforesaid step (a) and then 2.5 ml of acetic anhydride was added to the solution with stirring under ice-cooling. The mixture was allowed to rise to room temperature and after performing the reaction overnight, the reaction was further continued for 2 hours at 50° C. After ice-cooling the reaction mixture, 1 ml of water was added thereto. The reaction mixture was then allowed to stand for 2 hours at room temperature and concentrated at reduced pressure. The residue was purified in an ordinary manner to provide 3,23,2',4'-tetra-O-acetyl mycaminosyl tylonolide diethyl acetal.

(c). After dissolving the product obtained in aforesaid step (b) in 50 ml of methanol, the reaction was performed overnight at 50° C. to perform deacetylation at the 2',4'-position. The product obtained was subjected to chromatography using a silica gel (Kiesel gel 60 230-400 mesh) column and a chloroform-methanol solvent system to provide 1.05 g (yield of 94%) of 3,23-di-O-acetyl mycaminosyl tylonolide diethyl acetal.

The product showed the following physicochemical properties:

| (i) NMR (CDCl$_3$) | | | |
|---|---|---|---|
| δ (ppm) | H no. | Form | |
| 2.09 | 3 | s | 23-OCOCH$_3$ |
| 2.18 | 3 | s | 3-OCOCH$_3$ |
| 2.56 | 6 | s | N(CH$_3$)$_2$ |

(ii) Colorless amorphous solid (purified from acetone and n-hexane)
(iii) Anal. for C$_{39}$H$_{65}$NO$_{13}$:

| | C (%) | H (%) | N (%) |
|---|---|---|---|
| Calculated | 61.97 | 8.64 | 1.85 |
| Found | 62.15 | 8.59 | 1.88 |

(iv) $[\alpha]_D^{25}$: +3° (c 1.0, CHCl$_3$)

(v) UV $\lambda_{max}^{MeOH}$: 280 nm (ε = 22,000)

Rf 0.40 Wakogel B-5 chloroform-methanol (7:1)

EXAMPLE 2

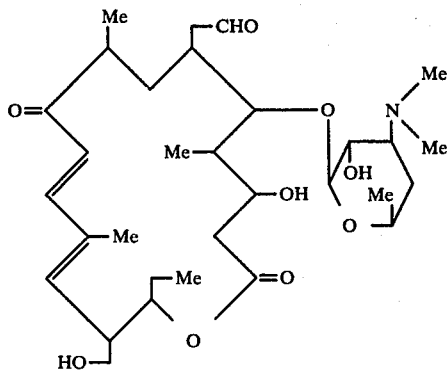

(a). After dissolving 489 mg of 3,23-di-O-methoxymethyl mycaminosyl tylonolide diethyl acetal in 9.8 ml of anhydrous pyridine, 185 mg of benzylsulfonyl chloride was slowly added to the solution with stirring at −40° C. followed by performing the reaction for 2 hours. Then, after adding thereto 0.02 ml of water at −40° C., the reaction was performed for 30 minutes at room temperature to decompose excessive benzylsulfonyl chloride and after concentrating the reaction mixture at reduced pressure, pyridine was azeotropically distilled with toluene. The residue was dissolved in chloroform and the solution was transferred to a separation funnel, washed once each with a saturated aqueous sodium hydrogencarbonate solution, a saturated aqueous sodium chloride solution, and water, dried by anhydrous sodium sulfate, and concentrated under reduced pressure to provide 3,23-di-O-methoxymethyl-4'-O-benzylsulfonyl mycaminosyl tylonolide diethyl acetal. Since the product was unstable, it was used in a subsequent reaction. The yield of the product was about 80%.

(b). In 12 ml of anhydrous methyl ethyl ketone was dissolved 588 mg of the product obtained in aforesaid step (a) and after adding thereto 145 mg of sodium iodide, the reaction was performed for 20 minutes at 80°

C. After the reaction was over, the reaction mixture was concentrated under reduced pressure and the residue formed was extracted with chloroform. The extract was washed once with a saturated aqueous sodium hydrogencarbonate solution, an aqueous 0.1 M sodium thiosulfate solution, and water, dried by anhydrous sodium sulfate, and then concentrated under reduced pressure. The residue was subjected to chromatography using a silica gel column and a cyclohexane-acetone (7:3) solvent system to provide 452 mg of 3,23-di-O-methoxymethyl-4'-deoxy-4'-iodo mycaminosyl tylonolide diethyl acetal.

(c). In 9 ml of anhydrous benzene was dissolved 452 mg of the product obtained in aforesaid step (b) and after adding thereto 445 mg of tri-n-butyltin hydride and then 8.2 mg of α,α'-azobisisobutyronitrile as a reaction initiator, the vessel was sealed under nitrogen stream and the reaction was performed for 2 hours at 80° C. The reaction mixture was concentrated under reduced pressure and the residue was developed on a column of 40 g of silica gel, and after eluting tri-n-butyltin compound with a cyclohexane-acetone (4:1) solvent system (emerging 250 ml thereof), the system was changed to a chloroform-methanol (9:1) solvent system, thereby 311 mg (yield of 82%) of 3,23-di-O-methoxymethyl-4'-deoxy mycaminosyl tylonolide diethyl acetal was obtained.

(d). After dissolving 45.5 mg of the product obtained in aforesaid step (c) in 0.23 ml of dioxane, 2.3 ml of an aqueous 10% trifluoroacetic acid solution was added to the solution and then the reaction was performed for 2 days at room temperature. After neutralizing the reaction mixture with 301 mg of sodium hydrogencarbonate, the product was extracted with chloroform. The extract was subjected to a chromatography by silica gel using chloroform-methanol-concentrated aqueous ammonia (8:1:0.1) solvent system to provide 26.0 mg (yield of 73%) of 4'-deoxy mycaminosyl tylonolide.

The product showed the following physicochemical properties:

| (i) NMR (CDCl₃) | | |
|---|---|---|
| δ (ppm) | H no. | Form |
| ~1.7 | ~2 | m | H'₄ |
| 2.31 | 6 | s | —N(CH₃)₂ |
| 9.80 | 1 | like s | —CHO |

(ii) Colorless amorphous solid (purified from acetone and n-hexane)
(iii) Anal. for $C_{31}H_{51}NO_9$:

| | C (%) | H (%) | N (%) |
|---|---|---|---|
| Calculated | 64.00 | 8.84 | 2.41 |
| Found | 63.72 | 8.81 | 2.21 |

(iv) $[\alpha]_D^{25}$: −12° (c 1.2, CHCl₃)

(v) UV $\lambda_{max}^{MeOH}$: 282.5 nm (ε = 21,000)

(vi) Rf 0.39 Wakogel B-5 chloroform-methanol (6:1)

In addition, 3,23-di-O-methoxymethyl mycaminosyl tylonolide diethyl acetal used in step (a) of this example was prepared by the following process.

REFERENCE EXAMPLE 2

(a). In 2.6 ml of acetonitrile was dissolved 510 mg of mycaminosyl tylonolide diethyl acetal and after performing the reaction with 0.16 ml of acetic anhydride for 30 minutes at room temperature, the reaction mixture was purified by an ordinary method (Quantitative).

(b). In 11.5 ml of anhydrous methylene chloride was dissolved 574 mg of 2,',4'-di-O-acetyl mycaminosyl tylonolide diethyl acetal obtained in aforesaid step (a) and after adding thereto 590 mg (6.80 ml) of diisopropylethylamine and 367 mg (0.34 ml) of chloromethyl ether, the reaction was performed for one day at room temperature. The reaction mixture obtained was poured in 29 ml of a saturated aqueous sodium hydrogencarbonate solution and the product was extracted with chloroform (Quantitative).

(c). After dissolving 641 mg of 3,23-di-O-methoxymethyl-2',4'-di-O-acetyl mycaminosyl tylonolide diethyl acetal in 30 ml of methanol, the reaction was performed overnight at 50° C., thereby the acetyl groups at the 2'- and 4'-positions were removed to provide 509 mg (yield of 88%) of 3,23-di-O-methoxymethyl mycaminosyl tylonolide diethyl acetal.

EXAMPLE 3

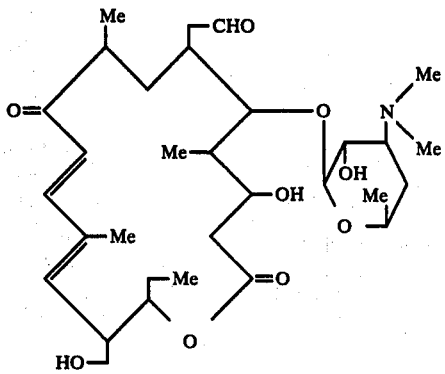

(a). By following the same procedure as in Example 2 using 1.08 g of 3,23-di-O-tetrahydrofuranyl mycaminosyl tylonolide diethyl acetal 14.5 mg (yield of 64%) of 4'-deoxy mycaminosyl tylonolide was obtained.

In addition 3,23-di-O-tetrahydrofuranyl mycaminosyl tylonolide diethylacetal used in this example was prepared by the following process.

REFERENCE EXAMPLE 3

(a). After dissolving 1.23 g of 2',4'-di-O-acetyl mycaminosyl tylonolide diethyl acetal in 25 ml of anhydrous methylene chloride, 0.62 of dihydrofuran and 492 mg of pyridine p-toluenesulfonate (PPTS) were added to the solution and the reaction was performed for 6 hours with stirring at 40° C. The reaction mixture was poured in 25 ml of a saturated aqueous sodium hydrogencarbonate solution and the product was extracted with methylene chloride. (Yield was quantitative).

(b). After dissolving 1.31 g of 3,23-di-O-tetrahydrofuranyl-2',4'-di-O-acetyl mycaminosyl tylonolide diethylacetal obtained in the above step (a) in 52 ml of methanol, the reaction was performed overnight at 50° C. The product was subjected to chromatography by a silica gel column using a chloroform-methanol (12:1) solvent system as a developer to provide 1.04 g (yield of 88%) of 3,23-di-O-tetrahydrofuranyl mycaminosyl tylonolide.

EXAMPLE 4

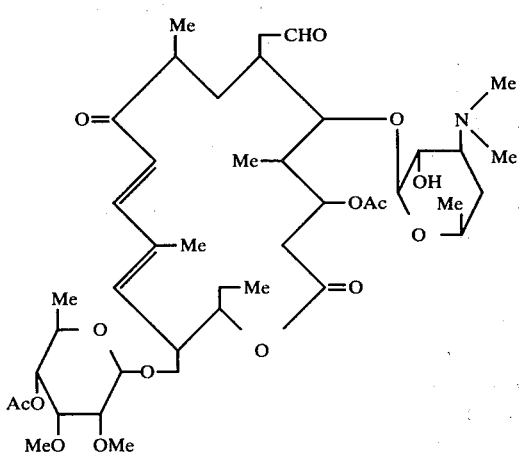

(a). In 27 ml of anhydrous pyridine was dissolved 1.32 g of 3,4″-di-O-acetyl demycarosyl tylosin diethyl acetal and after adding 406 mg of benzylsulfonyl chloride with stirring at −40° C. to the solution, the reaction was performed for 2 hours as it was. Then, after adding 0.05 ml of water to the reaction mixture, it was concentrated under reduced pressure and the residue was dissolved in chloroform. The solution was washed with a saturated aqueous sodium hydrogencarbonate solution and water, dried by anhydrous sodium sulfate, and concentrated under reduced pressure to provide 3,4″-di-O-acetyl-4′-benzylsulfonyl demycarosyl tylosin diethyl acetal.

Since the product was very unstable, it was used in the following reaction as it was.

(b). In 33 ml of anhydrous methyl ethyl ketone was dissolved 1.63 g of the product obtained in aforesaid step (a) and after adding thereto 338 mg of sodium iodide, the reaction was performed for 20 minutes at 75° C. After concentrating the reaction mixture under reduced pressure, the residue was extracted with chloroform. The crude product thus obtained was subjected to chromatography by a silica gel column using a cyclohexane-acetone (7:3) solvent system to provide 1.35 g (yield of 86%) of 3,4″-di-O-acetyl-4′-deoxy-4′-iodo demycarosyl tylosin diethyl acetal.

(c). After dissolving 1.18 g of the product obtained in aforesaid step (b) in 12 ml of anhydrous benzene and after adding thereto 990 mg of tri-n-butyltin hydride and then a catalytic amount of $\alpha,\alpha'$-azobisisobutyronitrile as a radical initiator, the reaction was performed for 3 hours at 75° C. The reaction mixture was concentrated under reduced pressure and the residue formed was applied to a silica gel column and after removing a tri-n-butyltin series material with a cyclohexane-acetone (4:1) solvent system, the solvent system was changed to a chloroform-methanol (7:1) solvent system, thereby 858 mg (yield of 83%) of 3,4″-di-O-acetyl-4′-deoxy demycarosyl tylosin diethyl acetate was obtained.

(d). After dissolving 56.0 mg of the product obtained in aforesaid step (c) in 1.2 ml of acetonitrile, 1.2 ml of an aqueous 0.1 N hydrochloric acid solution was added and the reaction was performed for one hour at room temperature. Then, after adding 1.5 ml of a saturated aqueous sodium hydrogencarbonate solution to the reaction mixture, the product was extracted with chloroform.

The extract was subjected to chromatography by a silica gel column using a chloroform-methanol-concentrated aqueous ammonia (30:1:0.1) solvent system to provide 48.7 mg (yield of 95%) of 3,4″-di-O-acetyl-4′-deoxy demycarosyl tylosin.

The product showed the following physicochemical properties.

| (i) NMR (CDCl$_3$) | | | |
|---|---|---|---|
| δ (ppm) | H no. | Form | |
| 2.11 | 6 | s | 3-OCOCH$_3$ / 4″-OCOCH$_3$ |
| 2.28 | 6 | s | 3′-N(CH$_3$)$_2$ |
| 9.73 | 1 | like s | —CHO |

| (ii) IR (KBr) | |
|---|---|
| WN (cm$^{-1}$) | |
| 1730 | —COO— |
| 1590 | —C=C—C=C— |

(iii) Colorless solid (reprecipitated from acetone and n-hexane)

(iv) Anal. C$_{45}$H$_{69}$NO$_{15}$:

| | C (%) | H (%) | N (%) |
|---|---|---|---|
| Calculated | 61.48 | 8.28 | 1.67 |
| Found | 61.43 | 8.16 | 1.54 |

(v) $[\alpha]_D^{23}$ +16° (c 0.5, CHCl$_3$)

(vi) UV $\lambda_{max}^{MeOH}$: 282 nm (ε = 24,000)

(vii) Rf 0.46 Wakogel B-5
chloroform-methanol-concd. aqueous ammonia (20:1:0.1)

In addition, the raw material, 3,4″-di-O-acetyl demycarosyl tylosin diethyl acetal used in step (a) of this example was prepared by the process of following Reference example.

REFERENCE EXAMPLE 4

(a). In 20 ml of anhydrous ethanol was dissolved in 1.94 g of tylosin and after adding thereto 411 mg of anhydrous p-toluenesulfonic acid with stirring under ice-cooling, the reaction was performed for one hour at room temperature. The reaction mixture obtained was neutralized by the addition of 0.44 ml of triethylamine and then concentrated under reduced pressure. Then, to the residue was added chloroform and a saturated aqueous sodium hydrogencarbonate solution and the mixture was shaken in a separating funnel. The chloroform layer obtained was washed with water and then concentrated under reduced pressure.

The residue was purified by a silica gel column chromatography using a chloroform-methanol-concentrated aqueous ammonia (20:1:0.1) solvent system to provide 1.34 g (yield of 75%) of demycarosyl tylosin diethyl acetal.

This product was also obtained by diethylacetalating (using 1.5 times molar amount of p-toluenesulfonic acid in absolute ethanol for 60 minutes at room temperature) demycarosyl tylosin obtained by acid-hydrolyzing (in an aqueous 0.2 N hydrochloric acid solution, for 60 minutes at 60° C.) tylosin. The yield was 79%.

(b). In 1 ml of anhydrous pyridine was dissolved 92 mg of demycarosyl tylosin diethyl acetal and after adding thereto 0.23 ml of acetic anhydride with stirring under ice-cooling, the reaction was performed for 2 days at 50° C. After adding 0.09 ml of water to the reaction mixture, it was concentrated under reduced pressure. The residue was dissolved in chloroform and the solution was washed with a saturated aqueous sodium hydrogencarbonate solution and then water, dried by anhydrous sodium sulfate, and concentrated under reduced pressure. The yield was quantitative.

(c). In 4.3 ml of methanol was dissolved 429 mg of 3,2',4',4''-tetra-O-acetyl demycarosyl tylosin diethyl acetal obtained in above step (b) and the reaction was performed overnight at 50° C. The reaction mixture was concentrated under reduced pressure, the residue was dissolved in chloroform, and the solution was washed with a saturated aqueous sodium hydrogencarbonate solution and then water, dried by anhydrous sodium sulfate, and concentrated under reduced pressure. The residue obtained was subjected to chromatography by a silica gel column using a chloroform-methanol-concentrated aqueous ammonia (30:1:0.1) solvent system to provide 376 mg (yield of 96%) of 3,4''-di-O-acetyl demycarosyl tylosin diethyl acetal.

EXAMPLE 5

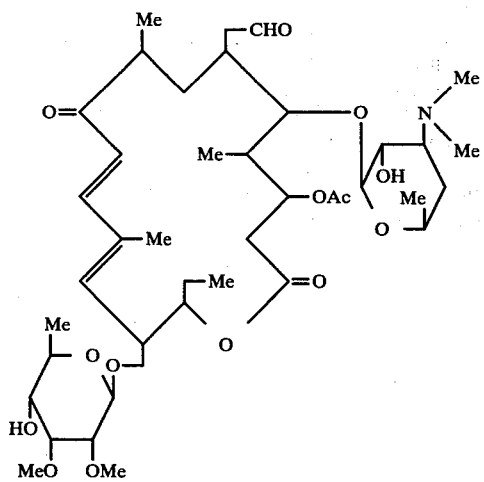

To 21.9 mg of 3,4''-di-O-acetyl-4'-deoxy demycarosyl tylosin was added 1.1 ml of water and after adding thereto 7.4 mg of p-toluenesulfonic acid mono-hydrate, the reaction was performed for one day at 60° C. After adding 1 ml of an aqueous saturated sodium hydrogencarbonate solution to the reaction mixture, the product was extracted with chloroform and the extract was washed with water, dried by anhydrous sodium sulfate, and concentrated under reduced pressure. Then, the residue obtained was purified using a silica gel column and a chloroform-methanol-concentrated aqueous ammonia solvent system to provide 11.2 mg (yield of 54%) of 3-O-acetyl-4'-deoxy demycarosyl tylosin.

The product showed the following physicochemical properties:

| (i) NMR (CDCl₃) | | | |
|---|---|---|---|
| δ (ppm) | H no. | Form | |
| 2.15 | 3 | s | 3-O—COCH₃ |
| 2.30 | 6 | s | 3'-N(CH₃)₂ |
| 9.72 | 1 | like s | ┌—CHO |

| (ii) IR (KBr) | |
|---|---|
| WN (cm⁻¹) | |
| 1730 | —COO— |
| 1590 | —C=C—C=C— |

-continued

| (iii) Colorless amorphous solid (re-precipitated from acetone and n-hexane) | | | |
|---|---|---|---|
| (iv) Anal. for C₄₁H₆₇NO₁₄: | | | |
| | C (%) | H (%) | N (%) |
| Calculated | 61.71 | 8.46 | 1.76 |
| Found | 61.39 | 8.52 | 1.64 |

(v) [α]$_D^{23}$: 0° (c 1.0, CHCl₃)

(vi) UV λ$_{max}^{MeOH}$: 282 nm (ε = 24,000)

(vii) Rf 0.39 Wakogel B-5
chloroform-methanol-concd. aqueous ammonia (20:1:0.1)

EXAMPLE 6

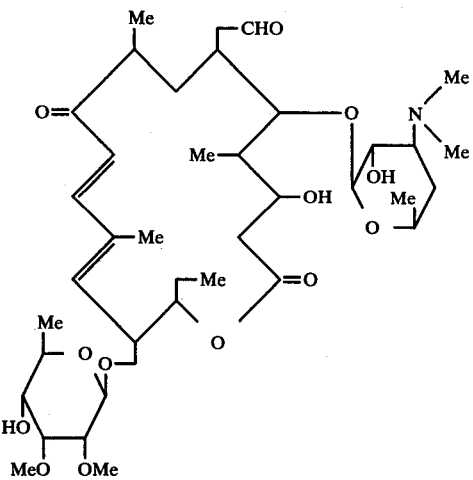

(a). After dissolving 660 mg of 3,4''-di-O-tetrahydrofuranyl demycarosyl tylosin diethyl acetal in 13 ml of anhydrous pyridine and cooling the solution to −35° C., 191 mg of benzylsulfonyl chloride was used to the mixture and the reaction was performed for one hour at the same temperature. After adding 0.024 ml of water, the reaction mixture was concentrated, the residue was dissolved in chloroform, and the solution was washed with a saturated aqueous sodium hydrogencarbonate solution and then water, dried by anhydrous sodium sulfate, and concentrated under reduced pressure to provide 3,4''-di-O-tetrahydrofuranyl-4'-benzylsulfonyl demycarosyl tylosin diethyl acetal.

(b). In 15.4 ml of anhydrous methyl ethyl ketone was dissolved 768 mg of the product obtained in aforesaid step (a) and after adding thereto 0.151 g of sodium iodide, the reaction was performed for 20 minutes at 75° C. The reaction mixture was concentrated and the residue was extracted with chloroform. The extract was washed with a mixture of a saturated aqueous sodium hydrogencarbonate solution and an aqueous 0.1 M sodium thiosulfate solution, and then water, dried by anhydrous sodium sulfate, and concentrated under reduced pressure.

The residue obtained was subjected to chromatography by a column of 38 g of silica gel using a cyclohexane-acetone (7:3) solvent system to provide 598 mg (yield of 81%) of 3,4'-di-O-tetrahydrofuranyl-4'-deoxy-4'-iodo demycarosyl tylosin diethyl acetal.

(c). In 4.9 ml of anhydrous benzene was dissolved 490 mg of the product obtained in aforesaid step (b) and after adding thereto 390 mg of tri-n-butyltin hydride and then a catalytic amount of azobisisobutyronitrile, the reaction was performed for one hour at 80° C. The crude product thus obtained was subjected to a chromatography by silica gel column using a cyclohexane-acetone (4:1) solvent system and then a chloroform-methanol (7:1) solvent system to provide 389 mg (yield of 90%) of 3,4''-di-O-tetrahydrofuranyl-4'-deoxy demycarosyl tylosin diethyl acetal.

(d). In 1.5 ml of acetonitrile was dissolved 77.0 mg of the product obtained in above step (c) and after adding thereto 2.38 ml of an aqueous 0.1 N hydrochloric acid solution under ice-cooling, the reaction was performed for one hour. Then, after adding 34 mg of sodium hydrogencarbonate to the reaction mixture, the product was extracted with chloroform and the extract was washed once with 1.5 ml of a saturated aqueous sodium sulfate solution, dried by anhydrous sodium sulfate, and concentrated under reduced pressure. The residue obtained was subjected to a chromatography by a silica gel column using a chloroform-methanol-concentrated aqueous ammonia (25:1:0.1) solvent system to provide 44.5 mg (yield of 74%) of 4'-deoxy demycarosyl tylosin.

The product showed the following physicochemical properties:

| (i) NMR (CDCl$_3$) | | | | |
|---|---|---|---|---|
| δ (ppm) | H no. | Form | J(Hz) | |
| 1.79 | 3 | s | | 12-CH$_3$ |
| 2.30 | 6 | s | | 3'-N(CH$_3$)$_2$ |
| 3.51 | 3 | s | | 2''-OCH$_3$ |
| 3.66 | 1 | s | | 3'''-OCH$_3$ |
| 4.21 | 1 | d$_{1',2'}$ | 7.5 | H'$_1$ |
| 4.59 | 1 | d$_{1'',2''}$ | 8.0 | H''$_1$ |
| 4.98 | 1 | m | | H$_{15}$ |
| 5.92 | 1 | d$_{13,14}$ | 10.5 | H$_{13}$ |
| 6.29 | 1 | d$_{10,11}$ | 16.0 | H$_{10}$ |
| 7.39 | 1 | d$_{11,10}$ | 16.0 | H$_{11}$ |
| 9.75 | 1 | like s | | —CHO |

(ii) IR (KBr)
WN (cm$^{-1}$)
1715 —COO—
1590 —C=C—C=C—

(iii) Colorless amorphous solid (re-precipitated from acetone and n-hexane)

(iv) Anal. for C$_{39}$H$_{65}$NO$_{13}$:

| | C (%) | H (%) | N (%) |
|---|---|---|---|
| Calculated | 61.97 | 8.67 | 1.85 |
| Found | 62.06 | 8.67 | 1.66 |

(v) [α]$_D^{23}$: −26° (c 0.5, CHCl$_3$)

(vi) UV λ$_{max}^{MeOH}$: 282 nm (ε = 26,000)

(vii) Rf 0.33 Wakogel B-5
chloroform-methanol-concd. aqueous ammonia (20:1:0.1)

In addition, the raw material, 3,4'''-di-O-tetrahydrofuranyl demycarosyl tylosin diethyl acetal used in above step (a) of the example was prepared by the process of the following reference example.

REFERENCE EXAMPLE 5

(a). In 20 ml of anhydrous acetonitrile was dissolved 2.20 g of demycarosyl tylosin diethyl acetal and after adding thereto 0.67 ml of acetic anhydride with stirring under ice-cooling, the mixture was stirred for one hour at room temperature. The reaction mixture was concentrated under reduced pressure, the residue was dissolved in chloroform, and the solution was washed with a saturated aqueous sodium hydrogencarbonate solution and then water, dried by anhydrous sodium sulfate, and concentrated under reduced pressure to provide 2',4'-di-O-acetyl demycarosyl tylosin diethyl acetal. The yield was quantitative.

(b). In 21.5 ml of anhydrous methylene chloride was dissolved 1.08 g of the product obtained in above step (a) and after adding thereto 0.44 ml of 2,3-dihydrofuran and 408 mg of pyridine p-toluenesulfonate (PPTS), the reaction was performed with stirring for 6 hours at 40° C. After adding the reaction mixture to 20 ml of a saturated aqueous sodium hydrogencarbonate solution, the product was extracted with chloroform to provide 3,4'''-di-O-tetrahydrofuranyl-2',4'-di-O-acetyl demycarosyl tylosin diethyl acetal. The yield was quantitative.

(e). In 56 ml of methanol was dissolved 1.13 g of the product obtained in above step (b) and the reaction was performed for 8 hours at 50° C. The reaction mixture was concentrated under reduced pressure and the residue was extracted with chloroform. Then, the extract was subjected to a chromatography by a silica gel column using a chloroform-methanol-concentrated aqueous ammonia (30:1:0.1) developing system to provide 860 mg (yield of 83%) of 3,4'-di-O-tetrahydrofuranyl demycarosyl tylosin diethyl acetal. (The amount of the product was, however, the sum of the four isomers by the tetrahydrofuranyl group).

EXAMPLE 7

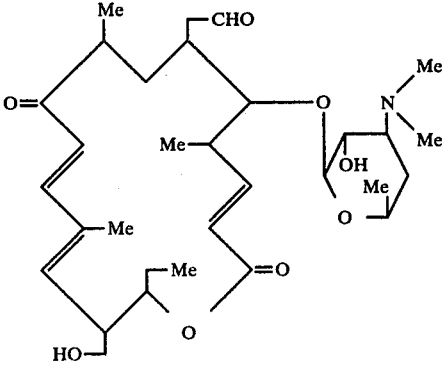

(a). In 1.54 ml of methanol was dissolved 154 mg of 3,23-di-O-acetyl-4'-deoxymycaminosyl tylonolide diethyl acetal and after adding thereto 2.31 ml of a concentrated aqueous ammonia, the reaction was performed for one day at room temperature. The reaction mixture obtained was concentrated under reduced pressure, the residue was dissolved in 7.5 ml of chloroform, and the solution was washed once each with 2.5 ml of a saturated aqueous sodium hydrogencarbonate solution, a saturated aqueous sodium chloride solution, and then water, dried by anhydrous sodium sulfate, and concentrated under reduced pressure.

Then, the residue obtained was subjected to chromatography by a silica gel column using a chloroform-methanol (10:1) solvent system and the fraction containing 3,23-didehydro-3,4'-dideoxy mycaminosyl tylonolide diethyl acetal was recovered. The amount of the product was 78.7 mg (yield of about 50%).

(b). After dissolving 35.0 mg of the product obtained in above step (a) in 0.7 ml of acetonitrile, 1.1 ml of a 0.1 N hydrochloric acid solution was added to the solution and the reaction was performed for 30 minutes. The product obtained was subjected to chromatography by a silica gel column using a chloroform-methanol-concentrated aqueous ammonia (11:1:0.1) solvent system to provide 2,23-didehydro-3,4'-dideoxy mycaminosyl tylonolide. The amount of the product was 22.7 mg (yield of 73%).

The product showed the following physicochemical properties:

| (i) | NMR (CDCl$_3$) | | | |
|---|---|---|---|---|
| | δ(ppm) | H no. | Form | J(Hz) |
| | ~1.7 | ~2 | m | | H'$_4$ |
| | 1.85 | 3 | s | | 12-CH$_3$ |
| | 2.30 | 6 | s | | —N(CH$_3$)$_2$ |
| | 3.20 | 1 | d,d$_{2',3'}^{1'}$ | 7.5 10.0 | H'$_2$ |
| | 3.76 | 2 | like d | 6.0 | H$_{23a,b}$ |
| | 4.20 | 1 | d$_{1',2'}$ | 7.5 | H'$_1$ |
| | 4.90 | 1 | m | | H$_{15}$ |
| | 5.83 | 1 | d$_{13,14}$ | ~10. (overlapped H$_2$) | H$_{13}$ |
| | 6.25 | 1 | d$_{10,11}$ | 16.0 | H$_{10}$ |
| | 6.87 | 1 | d,d$_{3,4}^{3,2}$ | 16.0 9.5 | H$_3$ |
| | 7.25 | 1 | d$_{11,10}$ | 16.0 | H$_{11}$ |
| | 9.80 | 1 | like s | | —CHO |

(ii) Colorless amorphous solid (purified from acetone and n-hexane)

(iii) Anal. for C$_{31}$H$_{49}$NO$_8$

| | C (%) | H (%) | N (%) |
|---|---|---|---|
| Calculated | 66.05 | 8.76 | 2.48 |
| Found | 65.77 | 8.73 | 2.29 |

(iv) [α]$_D^{25}$ 0° (c 0.5, CHCl$_3$)
    [α]$_D^{23}$ 0° (c 0.7, CHCl$_3$)

(v) UV λ$_{max}^{MeOH}$ 213.5 nm (ε = 23,000)
    285 nm (ε = 22,000)

(vi) Rf 0.44 Wakogel B-5 chloroform-methanol (6:1)

EXAMPLE 8

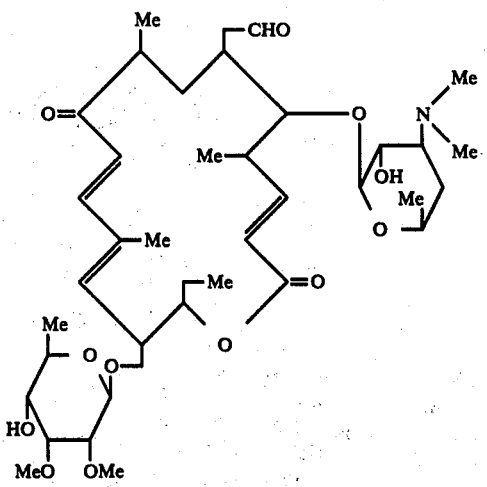

(a). After dissolving 534 mg of 3,4''-di-O-acetyl-4'-deoxy demycarosyl tylosin diethyl acetal in 5.3 ml of methanol, 5.3 ml of concentrated aqueous ammonia was slowly added to the solution and the reaction was performed overnight at room temperature. Then, the product obtained was subjected to chromatography by a silica gel column using a chloroform-methanol-concentrated aqueous ammonia (30:1:0.1) solvent system to provide 282 mg (yield of 59%) of 2,3-di-dehydro-3,4'-di-deoxy demycarosyl tylosin diethyl acetal.

(b). In 1.77 ml of acetonitrile was dissolved 71.8 mg of the product obtained in above step (a) and after adding thereto 1.77 ml of an aqueous 0.1 N hydrochloric acid solution with stirring under ice-cooling, the reaction was performed for one hour at room temperature. The product obtained was purified by a silica gel column using a chloroform-methanol-concentrated aqueous ammonia (25:1:0.1) solvent system to provide 59.9 mg (yield of 92%) of 2,3-di-dehydro-2,3'-di-deoxy demycarosyl tylosin.

The product showed the following physicochemical properties:

| (i) | NMR (CDCl$_3$) | | | |
|---|---|---|---|---|
| | δ(ppm) | H no. | Form | J(Hz) |
| | 1.83 | 3 | s | | 13-CH$_3$ |
| | 2.30 | 6 | s | | 3'-N(CH$_3$)$_2$ |
| | 3.52 | 3 | s | | 2''-OCH$_3$ |
| | 3.67 | 3 | s | | 3'''-OCH$_3$ |
| | 4.21 | 1 | d$_{1',2'}$ | 7.5 | H'$_1$ |
| | 4.60 | 1 | d$_{1'',2''}$ | 8.0 | H''$_1$ |
| | 5.85 | 1 | d$_{13,14}$ | 10.0 | H$_{13}$ |
| | 6.25 | 1 | d$_{10,11}$ | 15.5 | H$_{10}$ |
| | 6.88 | 1 | dd$_{3,4}^{3,2}$ | 15.5 9.5 | H$_3$ |
| | 7.27 | 1 | d$_{11,10}$ | 15.5 | H$_{11}$ |
| | 9.80 | 1 | like s | | —CHO |

(ii) Colorless amorphous solid (re-precipitated from acetone and n-hexane)

(iii) Anal. for C$_{39}$H$_{63}$NO$_{12}$

| | C (%) | H (%) | N (%) |
|---|---|---|---|
| Calculated | 63.48 | 8.61 | 1.90 |
| Found | 63.23 | 8.45 | 1.81 |

(iv) [α]$_D^{23}$ −16° (c 0.5, CHCl$_3$)

EXAMPLE 9

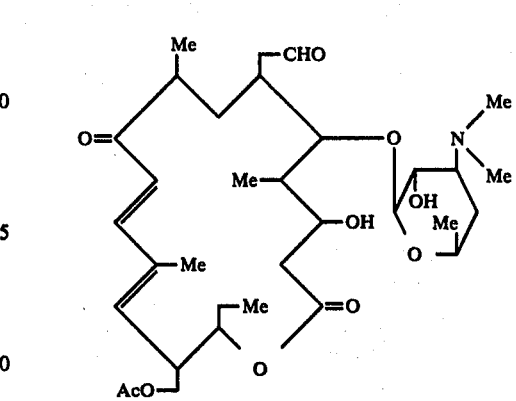

(a). In 7.3 ml of anhydrous ethanol was dissolved 182 mg of 3,23-di-O-tetrahydrofuranyl-4'-deoxy mycaminosyl tylonolide diethyl acetal and after adding thereto 69 mg of pyridinium p-toluenesulfonate, the reaction was performed for 3 hours at 78° C. The temperature of the reaction mixture was allowed cool to room temperature and after neutralizing it with 0.05 ml of triethylamine, the reaction mixture was concentrated under reduced pressure.

The residue obtained was dissolved in chloroform and the solution was washed with a saturated aqueous sodium hydrogencarbonate solution and a saturated aqueous sodium sulfate solution, dried by anhydrous sodium sulfate, and then concentrated under reduced pressure. Then, 135 mg of the crude product thus obtained was subjected to a chromatography by a silica gel column using a chloroform-methanol-aqueous ammonia (15:1:0.1) solvent system and the product was crystallized from acetone-n-hexane to provide 89.1 mg of 4'-deoxy mycaminosyl tylonolide diethyl acetal as the primary crystal.

(b). After dissolving 1.00 g of 4'-deoxy mycaminosyl tylonolide diethyl acetal in 5 ml of anhydrous acetonitrile, 188 mg of acetic anhydride was added to the solution and the reaction was performed for 2 hours. The product obtained was dissolved in chloroform and the solution was washed with a saturated aqueous sodium hydrogencarbonate solution and then water, dried by anhydrous sodium sulfate, and concentrated under reduced pressure.

Then, the product was recrystallized from a mixture of acetone and n-hexane to provide 990 mg (yield of 93%) of 2'-O-acetyl-4'-deoxy mycaminosyl tylonolide diethyl acetal as the primary crystal.

(c). After dissolving 122.5 mg of 2'-O-acetyl-4'-deoxy mycaminosyl tylonolide diethyl acetal in 1.2 ml of anhydrous pyridine, 27.6 mg (26.5 μliter) of acetyl chloride was added to the solution with stirring at −20° C. and the reaction was performed for 90 minutes. After adding thereto a small amount of water, the product was extracted with chloroform and the extract was washed with a saturated aqueous sodium hydrogencarbonate solution and then water, dried by anhydrous sodium sulfate, and concentrated under reduced pressure to provide 2',23-di-O-acetyl-4'-deoxy mycaminosyl tylonolide diethyl acetal.

For removing the acetyl group at the 2'-position, the product obtained was dissolved in 6 ml of methanol and the reaction was performed overnight at 50° C. The reaction mixture was concentrated under reduced pressure and the reside was dissolved in chloroform. Then, the solution was washed with a saturated aqueous sodium hydrogencarbonate solution and then a saturated aqueous sodium sulfate solution, dried by anhydrous sodium sulfate, and concentrated under reduced pressure.

Then, the residue obtained was subjected to chromatography by a column of 13 g of silica gel using a chloroform-methanol (12:1) solvent system to provide 119 mg (yield of 97%) of 23-O-acetyl-4'-deoxy mycaminosyl tylonolide diethyl acetal.

(d). After dissolving 71.3 mg of 23-O-acetyl-4'-deoxy mycaminosyl tylonolide diethyl acetal in 1.4 ml of acetonitrile, 2.0 ml of an aqueous 0.1 N hydrochloric acid solution was added to the solution and the reaction was performed for 60 minutes at room temperature. Then, after adding 25.7 mg of sodium hydrogencarbonate, the product was extracted with chloroform. The product obtained from the extract was recrystallized from a mixture of acetone and n-hexane to provide 58.1 mg (yield of 91%) of 23-O-acetyl-4'-deoxy mycaminosyl tylonolide.

The product showed the following physicochemical properties:

(i) NMR (CDCl₃)

| δ(ppm) | H no. | Form | J(Hz) | |
|---|---|---|---|---|
| 1.83 | 3 | s | | 12-CH₃ (H₂₂ × 3) |
| 2.10 | 3 | s | | 23-OCOCH₃ |
| 2.32 | 6 | s | | 3'-N(CH₃)₂ |
| 3.22 | 1 | dd₂',₃' | 7.5, 10.0 | H'₂ |
| 4.21 over- | } 3(sum) | like d₂₃,₁₄ | ~5 | H₂₃ₐ, ₐ' |
| 4.26 lapped | | d₁',₂' | 7.5 | H'₁ |
| 4.98 | 1 | m | | H₁₅ |
| 5.88 | 1 | broad d₁₃,₁₄ | 10.0 | H₁₃ |
| 6.38 | 1 | d₁₀,₁₁ | 16.0 | H₁₀ |
| 7.42 | 1 | d₁₁,₁₀ | 16.0 | H₁₁ |
| 9.85 | 1 | like s | | —CHO (H₂) |

(ii) Colorless prism-like crystal (acetone and n-hexane)
(iii) m. p. 106–108° C. (fine melting point measuring device, correction of the m. p. was not made) (melted)
(iv) Anal. for C₃₃H₅₃NO₁₀·2H₂O

| | C (%) | H (%) | N (%) |
|---|---|---|---|
| Calculated | 60.07 | 8.71 | 2.12 |
| Found | 59.98 | 8.96 | 2.05 |

(v) [α]$_D^{19}$ −12° (c 1.0, CHCl₃)
(vi) UV λ$_{max}^{MeOH}$ 281 nm (ε = 22,000)
(vii) Rf 0.37 Wakogel B-5 chloroform-methanol (10:1)

EXAMPLE 10

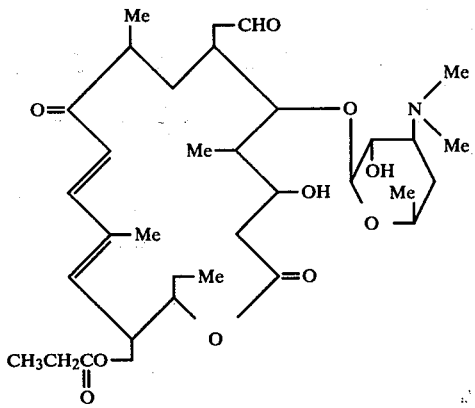

(a). In 1.1 ml of anhydrous pyridine was dissolved 105.7 mg of 2'-O-acetyl-4'-deoxy mycaminosyl tylonolide diethyl acetal prepared by step (a) and step (b) of Example 9 and after adding thereto 28.1 mg of propionyl chloride with stirring at −20° C., the reaction was performed for 90 minutes. After adding a small amount of water to the reaction mixture, the temperature of the mixture was allowed to rise to room temperature.

The reaction mixture was concentrated under reduced pressure and the product obtained was extracted with chloroform.

Then, for removing the acetyl group at the 2'-position, the product obtained was dissolved in 5.3 ml of methanol and the reaction was performed overnight at 50° C. The reaction mixture was, then, concentrated under reduced pressure, the residue was dissolved in 5.3 ml of chloroform, and the solution was washed with a saturated aqueous sodium hydrogencarbonate solution and then water, dried by anhydrous sodium sulfate, and concentrated under reduced pressure. The residue was subjected to a chromatography by a silica gel column using a chloroform-methanol (12:1) solvent system to provide 100.6 mg (yield of 93%) of 23-O-propionyl-4'-deoxy mycaminosyl tylonolide diethyl acetal.

(b). After dissolving 63.3 mg of the product obtained in above step (a) in 1.3 ml of acetonitrile, 1.8 ml of an aqueous 0.1 N hydrochloric acid solution was added to the solution and the reaction was performed for 60 minutes at room temperature. After adding 22.9 mg of a sodium hydrogencarbonate powder to the reaction mixture, the product was extracted with chloroform.

The product obtained was subjected to chromatography by a silica gel column using a chloroform-methanol (9:1) solvent system to provide 50.8 mg (yield of 90%) of 23-O-propionyl-4'-deoxy mycaminosyl tylonolide.

The product showed the following physicochemical properties:

| (i) | NMR (CDCl$_3$) | | | |
|---|---|---|---|---|
| | $\delta$(ppm) | H no. | Form | J(Hz) |
| | 2.32 | 6 | s | | 3'-N(CH$_3$)$_2$ |
| near | 2.4 | — | — | | 23-O—COCH$_2$CH$_3$ |
| | 4.20 over- | ⎫ | like d$_{23,14}$ | ~5 | H$_{23a,a'}$ |
| | | ⎬ 3(sum) | | | |
| | 4.25 lapped | ⎭ | d$_{1',2'}$ | 7.5 | H'$_1$ |
| | 4.98 | 1 | m | | H$_{15}$ |
| | 5.87 | 1 | broad d$_{13,14}$ | 10.0 | H$_{13}$ |
| | 6.37 | 1 | d$_{10,11}$ | 16.0 | H$_{10}$ |
| | 7.41 | 1 | d$_{11,10}$ | 16.0 | H$_{11}$ |
| | 9.83 | 1 | like s | | ⌐CHO (H$_{20}$) |

(ii) Colorless amorphous solid (acetone and n-hexane)
(iii) Anal. for C$_{34}$H$_{55}$NO$_{10}$

| | C (%) | H (%) | N (%) |
|---|---|---|---|
| Calculated | 64.03 | 8.69 | 2.20 |
| Found | 63.82 | 8.53 | 2.04 |

(iv) $[\alpha]_A^{19}$ —6° (c 1.0, CHCl$_3$)
(v) UV $\lambda_{max}^{MeOH}$ 281 nm ($\epsilon$ = 25,000)
(vi) Rf 0.39 Wakogel B-5 chloroform-methanol (9:1).

The product showed the following physicochemical properties:

| (i) | NMR (CDCl$_3$) | | | |
|---|---|---|---|---|
| | $\delta$(ppm) | H no. | Form | J(Hz) |
| | 0.96 | | t | 7.0 | 15-CH$_2$CH$_3$(H$_{17}$) |
| | 0.96(*) | 6 | " | " | 23-O—COCH$_2$CH$_3$ |
| | 1.67 | ~2 | m | | 23-O—COCH$_2$CH$_3$ |
| | 2.31 | 6 | s | | 3'-N(CH$_3$)$_2$ |
| near | 2.3 | ~2 | — | | 23-O—COCH$_2$CH$_3$ |
| | 9.81 | 1 | like s | | ⌐CHO (H$_{20}$) |

(ii) Colorless amorphous solid (acetone and n-hexane)
(iii) Anal. for C$_{35}$H$_{57}$NO$_{10}$

| | C (%) | H (%) | N (%) |
|---|---|---|---|
| Calculated | 64.49 | 8.81 | 2.15 |
| Found | 64.37 | 8.70 | 2.03 |

(iv) $[\alpha]_D^{19}$ —9° (c 1.0, CHCl$_3$)
(v) Rf 0.38 Wakogel B-5 chloroform-methanol (9:1)

(*)same position

EXAMPLE 11

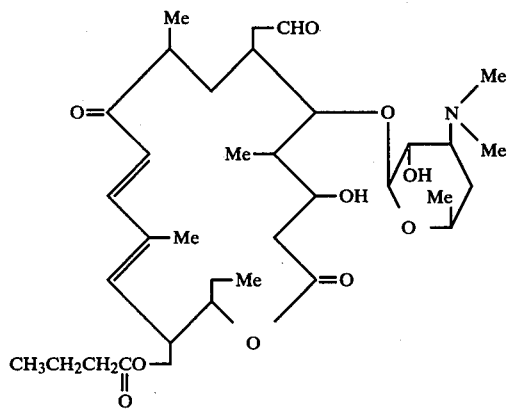

By following the same procedure as in Example 10 using 109.1 mg of 2'-O-acetyl-4'-deoxy mycaminosyl tylonolide diethyl acetal prepared by the process of step (a) and step (b) of Example 9 and 33.4 mg of n-butyryl chloride, 23-O-n-butyryl-4'-deoxy mycaminosyl tylonolide was obtained. The amount was 59.1 mg (yield of 94%).

EXAMPLE 12

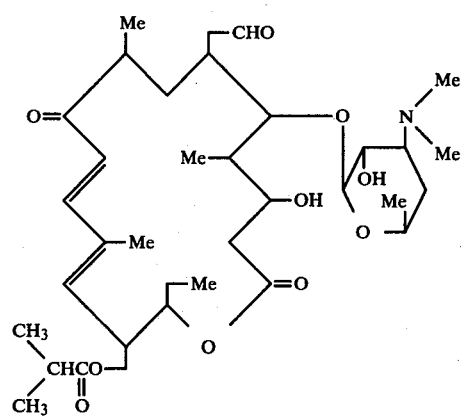

By following the same procedure as in Example 10 using 104.7 mg of 2'-O-acetyl-4'-deoxy mycaminosyl tylonolide diethyl acetal prepared by the process of step (a) and step (b) of Example 9 and 32 mg of iso-butyryl chloride, 23-O-iso-butyryl-4'-deoxy mycaminosyl tylonolide was obtained. The amount was 47.9 mg (yield of 92%).

The product showed the following physicochemical properties:

| (i) | NMR (CDCl₃) | | | |
|---|---|---|---|---|
| δ(ppm) | H no. | Form | J(Hz) | |
| 1.18 | 6 | d | 7.0 | 23-O—COCH(CH₃)₂ |
| 1.82 | 3 | s | | 12-CH₃ (H₂₂ × 3) |
| 2.31 | 6 | s | | 3'-N(CH₃)₂ |
| 3.23 | 1 | dd$_{2',3'}^{2',1'}$ | 7.5 10.0 | H'₂ |
| 4.19 | 2 | like d₂₃,₁₄ | ~5 | H₂₃ |
| 4.23 | 1 | d₁',₂' | 7.5 | H'₁ |
| 4.98 | 1 | m | | H₁₅ |
| 5.85 | 1 | broad d₁₃,₁₄ | 10.0 | H₁₃ |
| 6.38 | 1 | d₁₀,₁₁ | 16.0 | H₁₀ |
| 7.40 | 1 | d₁₁,₁₀ | 16.0 | H₁₁ |
| 9.82 | 1 | like s | | ⌐CHO (H₂₀) |

| (ii) | Colorless amorphous solid (acetone and n-hexane) | | | |
|---|---|---|---|---|
| (iii) | Anal. for C₃₅H₅₇NO₁₀ | | | |
| | | C (%) | H (%) | N (%) |
| | Calculated | 64.49 | 8.81 | 2.15 |
| | Found | 64.25 | 8.57 | 2.08 |
| (iv) | [α]$_D^{19}$ | −6° | (c 1.0, CHCl₃) | |
| (v) | UV | λ$_{max}^{MeOH}$ | 281 nm | (ε = 22,000) |
| (vi) | Rf | 0.41 | Wakogel B-5 chloroform-methanol (10:1) | |

EXAMPLE 13

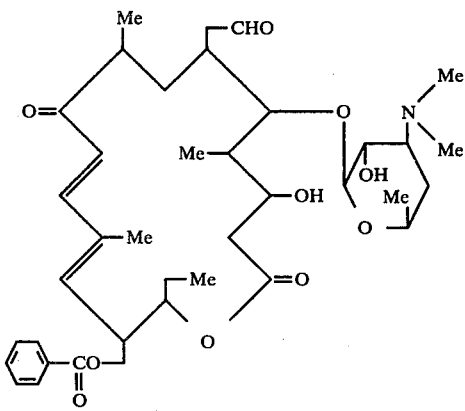

(a). In 7.3 ml of anhydrous ethanol was dissolved 182 mg of 3,23-di-O-tetrahydrofuranyl-4'-deoxy mycaminosyl tylonolide diethyl acetal and after adding thereto 69 mg of pyridinium p-toluenesulfonate, the reaction was performed for 3 hours at 78° C. The reaction mixture was neutralized with 0.05 ml of triethylamine and concentrated under reduced pressure.

The crude product obtained was subjected to chromatography by a silica gel column using a chloroform-methanol-concentrated aqueous ammonia (15:1:0.1) solvent system and the product obtained was crystallized from a mixture of acetone and n-hexane to provide 89.1 mg of 4'-deoxy mycaminosyl tylonolide diethyl acetal as the primary crystal.

(b). After dissolving 1.00 g of the product obtained in above step (a) in 5 ml of anhydrous acetonitrile, 188 mg of acetic anhydride was added to the solution and the reaction was performed for 2 hours. The reaction mixture was concentrated under reduced pressure, the residue was dissolved in chloroform, and the solution was washed with a saturated aqueous sodium hydrogencarbonate solution and then water, dried by anhydrous sodium sulfate, and concentrated under reduced pressure. The product was recrystallized from a mixture of acetone and n-hexane to provide 990 mg (yield of 93%) of 2'-O-acetyl-4'-deoxy mycaminosyl tylonolide diethyl acetal as the primary crystal.

(c). After dissolving 102.8 mg of the product obtained in above step (b) in 1.0 ml of anhydrous pyridine, 41.3 mg (34.2 μliter) of benzoyl chloride was added to the solution with stirring at −30° C. and the reaction was performed for 15 minutes. Then, for decomposing excessive benzoyl chloride, a small amount of water was added to the reaction mixture and the temperature thereof was allowed to rise to room temperature. The reaction mixture was concentrated under reduced pressure, the residue was dissolved in chloroform, and the solution was washed with a saturated aqueous sodium hydrogencarbonate solution and then water, dried by anhydrous sodium sulfate, and concentrated under reduced pressure to provide 2'-O-acetyl-23-O-benzoyl-4'-deoxy mycaminosyl tylonolide diethyl acetal.

Then, for removing the acetyl group at the 2'-position, the product was dissolved in 5.2 ml of methanol and the reaction was performed overnight at 50° C. The reaction mixture was concentrated under reduced pressure, the residue was dissolved in chloroform, and the solution was washed with a saturated aqueous sodium hydrogencarbonate solution and a saturated aqueous sodium sulfate solution, dried by anhydrous sodium sulfate, and concentrated under reduced pressure.

The residue was subjected to a chromatography by a silica gel column using a chloroform-methanol (12:1) solvent system to provide 109.8 mg (yield of 99%) of 23-O-benzoyl-4'-deoxy mycaminosyl tylonolide diethyl acetal.

(d). In 1.3 ml of acetonitrile was dissolved 65.2 mg of the product obtained in above step (c) and after adding thereto 1.7 ml of an aqueous 0.1 N hydrochloric acid solution and the reaction was performed for 60 minutes. After adding 22 mg of sodium hydrogencarbonate to the reaction mixture, the product was extracted with chloroform and the extract was washed with a saturated aqueous sodium chloride solution and a saturated aqueous sodium sulfate solution, dried by anhydrous sodium sulfate, and concentrated under reduced pressure.

The residue was subject to chromatography by a silica gel column using a chloroform-methanol (12:1) solvent system to provide 54.8 mg (yield of 93%) of 23-O-benzoyl-4'-deoxy mycaminosyl tylonolide.

The product showed the following physicochemical properties:

| (i) NMR (CDCl₃) | | | | |
|---|---|---|---|---|
| δ(ppm) | H no. | Form | J(Hz) | |
| 2.30 | 6 | s | | 3'-N(CH₃)₂ |
| 4.23 | 1 | d₁',₂' | 7.5 | H₁' |
| 5.10 | 1 | m | | H₁₅ |
| 5.97 | 1 | broad d₁₃,₁₄ | 10.0 | H₁₃ |
| 6.38 | 1 | d₁₀,₁₁ | 16.0 | H₁₀ |
| near 7.6 | 3 | m | | |
| | | | | 23-OCO—⌐⌐ |
| near 8.1 | 2 | m | | |
| 9.82 | 1 | like d | | ⌐CHO(H₂₀) |

-continued (ii) Colorless amorphous solid (acetone and n-hexane)
(iii) Anal. for $C_{38}H_{55}NO_{10}$:

|  | C (%) | H (%) | N (%) |
|---|---|---|---|
| Calculated: | 66.55 | 8.08 | 2.04 |
| Found: | 66.26 | 8.06 | 1.94 |

(iv) $[\alpha]_D^{19}: -19°$ (c 1.0, $CHCl_3$)
(v) UV $\lambda_{max}^{MeOH}$: 230 nm ($\epsilon = 20,000$)
   $\lambda_D^{MeOH}$: 281 nm ($\epsilon = 25,000$)
(vi) Rf 0.44 Wakogel B-5
   chloroform-methanol (9:1)

EXAMPLE 14

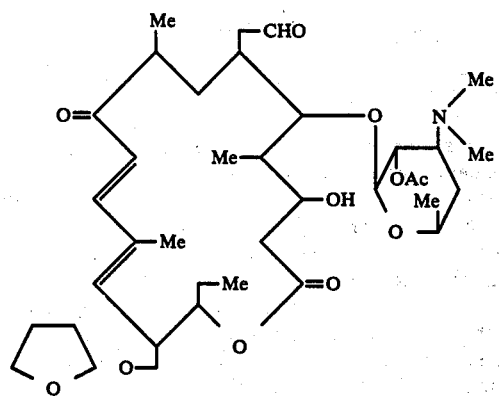

After dissolving 52.4 mg of 2'-O-acetyl-4'-deoxy mycaminosyl tylonolide in 1.1 ml of methylene chloride, 11.8 mg of 2,3-dihydrofuran and 31.6 mg of pyridinium p-toluenesulfonate were added to the solution and the reaction was performed for 26 hours at room temperature.

The reaction mixture was rendered weakly basic by vigorously stirring it together with a saturated aqueous sodium hydrogencarbonate solution and the methylene chloride layer formed was recovered, washed with 1 ml of a saturated aqueous sodium chloride solution and then water, dried by anhydrous sodium sulfate, and concentrated under reduced pressure to provide 23-O-tetrahydrofuranyl-2'-O-acetyl-4'-deoxy mycaminosyl tylonolide.

EXAMPLE 15

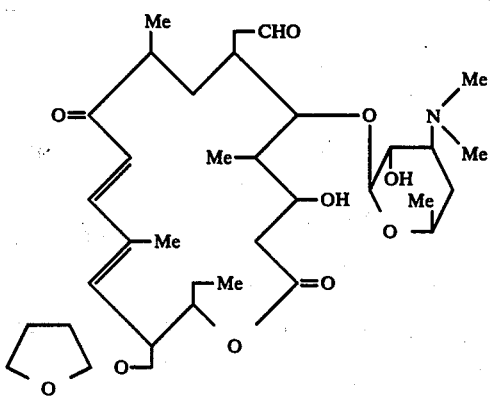

In 2.6 ml of methanol was dissolved 23-O-tetrahydrofuranyl-2'-O-acetyl-4'-deoxy mycaminosyl tylonolide obtained in Example 14 and the reaction was performed for 6 hours at 50° C.

The crude product obtained was subjected to a chromatography by a silica gel column using a chloroform-methanol (12:1) solvent system to provide 40.3 mg (yield of 74%) of 23-O-tetrahydrofuranyl-4'-deoxy mycaminosyl tylonolide.

The product showed the following physicochemical properties:

(i) NMR ($CDCl_3$)

| $\delta$(ppm) | H no. | Form | J(Hz) | Reversion |
|---|---|---|---|---|
| ~1.7 | ~2 | m | | $H_{4'}$ |
| 1.81 | 3 | s | | $H_{22}(12-CH_3)$ |
| ~1.91 | 4 | m | | (THF ring) |
| 2.30 | 6 | s | | $3'-N(CH_3)_2$ |
| 5.90 } | 1(sum) | broad $d_{13,14}$ | 10.0 | $H_{13}$ |
| 5.99 } | | broad $d_{13,14}$ | 10.0 | |

*: The product was a mixture of two kinds of isomers by a tetrahydrofruanyl group, which was clearly recognized as the signal of $H_{13}$ only in the NMR.

(ii) Colorless amorphous solid (acetone and hexane)
(iii) Anal. for $C_{35}H_{57}NO_{10}$:

|  | C (%) | H (%) | N (%) |
|---|---|---|---|
| Calculated: | 64.49 | 8.81 | 2.15 |
| Found: | 64.42 | 8.75 | 2.14 |

(iv) $[\alpha]_D^{19}: -25°$ (c 1.0, $CHCl_3$)
(v) UV $\lambda_{max}^{MeOH}$: 282 nm ($\epsilon = 27,000$)
(vi) Rf 0.30 Wakogel B-5
   chloroform-methanol (10:1)

EXAMPLE 16

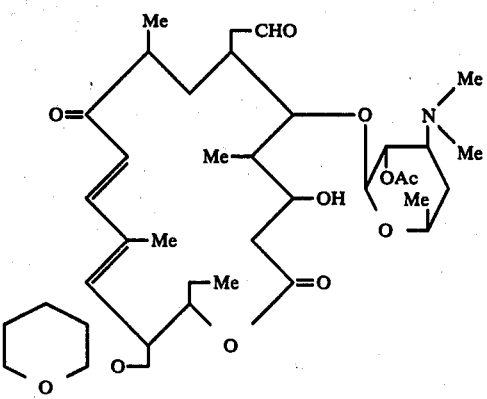

In 1 ml of anhydrous methylene chloride was dissolved 51.3 mg of 23-O-acetyl-4'-deoxy mycaminosyl tylonolide and after adding thereto 13.9 mg of 2,3-dihydropyran and 30.9 mg of pyridinium p-toluenesulfonate, the reaction was performed for 24 hours at 40° C.

The reaction mixture was rendered weak basic by vigorously stirring it together with a saturated aqueous sodium hydrogencarbonate solution and the methylene chloride layer formed was recovered, washed with a saturated aqueous sodium chloride solution and then water, dried by anhydrous sodium sulfate, and concentrated under reduced pressure to provide 23-O-tetrahydropyranyl-2'-O-acetyl-4'-deoxy mycaminosyl tylonolide.

EXAMPLE 17

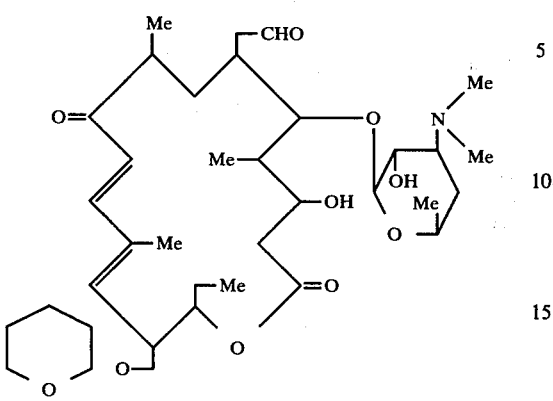

In 2.6 ml of methanol was dissolved 23-O-tetrahydropyranyl-2'-O-acetyl-4'-deoxy mycaminosyl tylonolide obtained in Example 16 and the reaction was performed for 6 hours at 50° C.

The reaction mixture was concentrated under reduced pressure, the residue was dissolved in chloroform, and the solution was washed with a saturated aqueous sodium hydrogencarbonate solution and a saturated aqueous sodium sulfate solution, dried by anhydrous sodium sulfate, and concentrated under reduced pressure.

The residue obtained was subjected to chromatography by a silica gel column using a chloroform-methanol (12:1) solvent system to provide 38.9 mg (yield of 70%) of 23-O-tetrahydropyranyl-4'-deoxy mycaminosyl tylonolide.

The product showed the following physicochemical properties:

(i) NMR (CDCl$_3$)

| δ(ppm) | H no. | Form | J(Hz) | |
|---|---|---|---|---|
| ~1.7 | ~8 | m | | 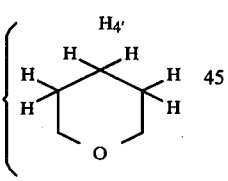 |
| 2.30 | 6 | s | | 3'-N(CH$_3$) |
| 4.58 | 1 | narrow m | | 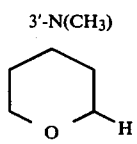 |
| 5.97 | 1 | broad d$_{13,14}$ | 10.0 | H$_{13}$ |
| 6.34 | 1 | d$_{10,11}$ | 16.0 | H$_{10}$ |
| 7.40 | 1 | d$_{11,10}$ | 16.0 | H$_{11}$ |
| 9.80 | 1 | like s | | H$_{20}$ |

(ii) Colorless amorphous solid (acetone and n-hexane)

(iii) Anal. for C$_{36}$H$_{59}$NO$_{10}$:

| | C (%) | H (%) | N (%) |
|---|---|---|---|
| Calculated: | 64.94 | 8.93 | 2.10 |
| Found: | 64.92 | 8.85 | 2.14 |

(iv) $[\alpha]_D^{19}$: $-17°$ (c 1.0, CHCl$_3$)

(v) UV $\lambda_{max}^{MeOH}$: 282.5 nm (ε = 27,000)

(vi) Rf 0.38 Wakogel B - 5 chloroform-methanol (10:1)

EXAMPLE 18

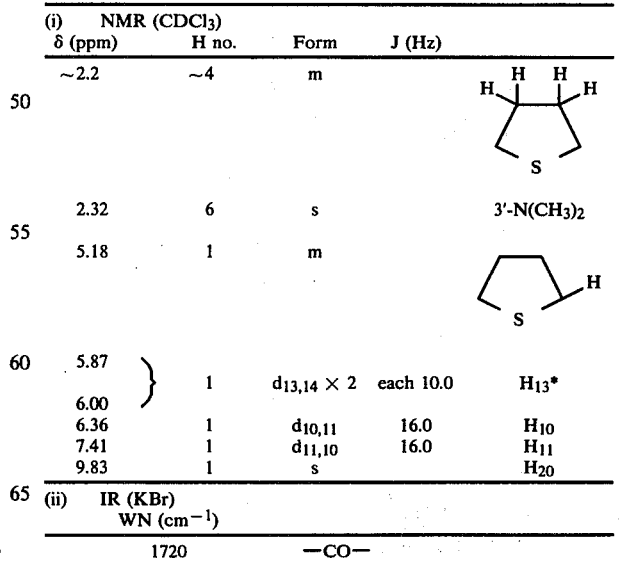

After dissolving 64.5 mg of 2'-O-acetyl-4'-deoxy mycaminosyl tylonolide in 1.3 ml of anhydrous methylene chloride, 80.7 mg of 2-benzoyloxytetrahydrothiofuran and 25.0 mg of p-were added and then the reaction was performed for 40 minutes. After adding 1.3 ml of a saturated aqueous sodium hydrogencarbonate solution to the reaction mixture followed by stirring, the methylene chloride layer was recovered, washed with water, dried by anhydrous sodium sulfate, and concentrated under reduced pressure.

Then, for removing the acetyl group at the 2'-position, 3.2 ml of methanol was added to the reaction product and the reaction was performed for 6 hours at 50° C. The reaction mixture was concentrated under reduced pressure, the residue was dissolved in chloroform, and the solution was washed with a saturated aqueous sodium hydrogencarbonate solution and a saturated aqueous sodium sulfate solution, dried by anhydrous sodium sulfate, and concentrated under reduced pressure. The residue was subjected to chromatography by a silica gel column using a chloroform-methanol (9:1) solvent system to provide 48.0 mg (yield of 74%) of 23-O-tetrahydrothiofuranyl-4'-deoxy mycaminosyl tylonolide.

The product showed the following physicochemical properties:

(i) NMR (CDCl$_3$)

| δ (ppm) | H no. | Form | J (Hz) | |
|---|---|---|---|---|
| ~2.2 | ~4 | m | | 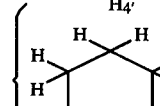 |
| 2.32 | 6 | s | | 3'-N(CH$_3$)$_2$ |
| 5.18 | 1 | m | | 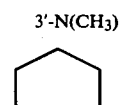 |
| 5.87 / 6.00 | 1 | d$_{13,14}$ × 2 | each 10.0 | H$_{13}$* |
| 6.36 | 1 | d$_{10,11}$ | 16.0 | H$_{10}$ |
| 7.41 | 1 | d$_{11,10}$ | 16.0 | H$_{11}$ |
| 9.83 | 1 | s | | H$_{20}$ |

(ii) IR (KBr) WN (cm$^{-1}$)

| 1720 | —CO— |
|---|---|

-continued

| | |
|---|---|
| 1690 | ⟩CO (α,β,γ,δ unsaturated) |
| 1595 | —C=C—C=C— |

(iii) Colorless amorphous solid (acetone and n-hexane)
(iv) Anal. for $C_{35}H_{57}NO_9S$:

| | C (%) | H (%) | N (%) | S (%) |
|---|---|---|---|---|
| Calculated | 62.94 | 8.60 | 2.10 | 4.80 |
| Found | 62.63 | 8.64 | 2.28 | 4.56 |

(v) $[\alpha]_D^{20}$: −24° (c 1.0, $CHCl_3$)
(vi) UV $\lambda_{max}^{MeOH}$: 283 nm (ε = 23,000)
(vii) Rf 0.38 Walogel B-5 chloroform-methanol (9:1).

*It is considered to be caused by the bonding mode (perhaps α,β) of the tetrahydrothiofuranyl group.

EXAMPLE 19

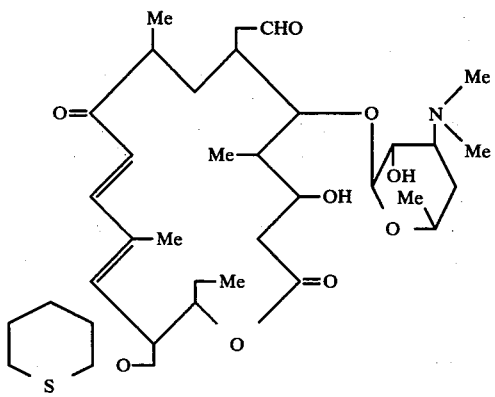

After dissolving 64.3 mg of 2'-O-acetyl-4'-deoxy mycaminosyl tylonolide in 1.3 ml of anhydrous methylene chloride, 85.9 mg of 2-benzoyloxytetrahydrothiopyran and then 24.9 mg of p-TsOH were added to the solution with stirring at room temperature and the reaction was performed for 80 hours at the same temperature. After adding 1.3 ml of a saturated aqueous sodium hydrogencarbonate solution to the reaction mixture followed by stirring quickly, the methylene chloride layer was recovered. The aqueous layer was extracted twice each time with 1.3 ml of methylene chloride. These methylene chloride layers were combined with each other, washed twice each with 1.3 ml of water, dried by anhydrous sodium sulfate, and concentrated under reduced pressure.

Then, for removing the acetyl group at the 2'-position, the product was dissolved in 3.2 ml of methanol and the reaction was performed for 6 hours at 50° C. The reaction mixture was concentrated under reduced pressure, the residue was dissolved in chloroform, and the solution was washed with a saturated aqueous sodium hydrogencarbonate solution and a saturated aqueous sodium sulfate solution, dried by anhydrous sodium sulfate and concentrated under reduced pressure. The residue obtained was subjected to chromatography by a silica gel column using a chloroform-methanol (9:1) solvent system to provide 45.0 mg (yield of 68%) of 23-O-tetrahydrothiopyranyl-4'-deoxy mycaminosyl tylonolide.

The product showed the following physicochemical properties:

(i) NMR ($CDCl_3$)

| δ (ppm) | H no. | Form | J (Hz) | |
|---|---|---|---|---|
| ~2 | ~6 | m | | (cyclohexane-like ring with S) |
| 2.31 | 6 | s | | 3'-N(CH$_3$)$_2$ |
| 4.44 | 1 | m | | (ring with S, H) |
| 6.00 / 6.07 | 1 | $d_{13,14} \times 2$ | each 10.0 | $H_{13}$* |

(ii) Colorless amorphous solid (acetone and n-hexane)
(iii) Anal. for $C_{36}H_{59}NO_9S$:

| | C (%) | H (%) | N (%) | S (%) |
|---|---|---|---|---|
| Calculated | 63.41 | 8.72 | 2.05 | 4.70 |
| Found | 63.17 | 8.65 | 1.94 | 4.47 |

(iv) $[\alpha]_D^{20}$: −18° (c 1.0, $CHCl_3$)
(v) UV $\lambda_{max}^{MeOH}$: 283 nm (ε = 21,000)
(vi) Rf 0.37 Wakogel B-5 chloroform-methanol (9:1).

*It is considered to be caused by the bonding mode (perhaps α,β) of the tetrahydrothiopyranyl group.

EXAMPLE 20

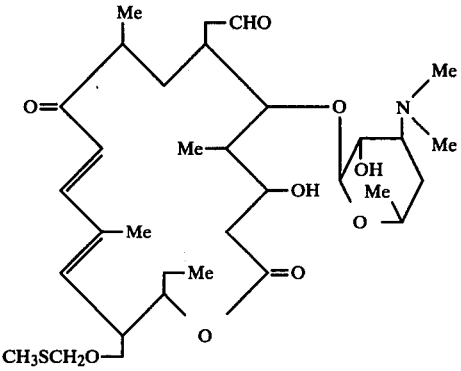

After dissolving 82.2 mg of 2'-O-acetyl-4'-deoxy mycaminosyl tylonolide in 1.02 ml of dimethyl sulfoxide, 0.2 ml of acetic acid and 15.1 mg of trifluoroacetic acid were added to the solution and after further adding thereto 336 mg of acetic anhydride, the reaction was performed for 13 hours at room temperature (15°–80° C.). The reaction mixture was poured into ice-water containing 1.3 g of sodium hydrogencarbonate and the mixture was stirred for 30 minutes. Then, chloroform was added to the mixture to cause phase separation and the chloroform layer was recovered. The aqueous layer was also recovered and extracted twice each time with 5 ml of chloroform. These chloroform layers were combined with each other, washed once with 5 ml of a saturated aqueous sodium chloride solution and then four times each time with 5 ml of a saturated aqueous sodium sulfate solution, dried by anhydrous sodium sulfate, and concentrated under reduced pressure.

The residue obtained was dissolved in 4 ml of methanol and the reaction was performed for 6 hours at 50° C. The reaction mixture was concentrated and the residue was dissolved in chloroform. The solution was washed with a saturated aqueous sodium hydrogencarbonate solution and a saturated aqueous sodium sulfate solution, dried by anhydrous sodium sulfate and concentrated under reduced pressure.

The residue obtained was subjected to chromatography by a column of 10 g of silica gel using a chloroform-methanol-concentrated aqueous ammonia (25:1:0.1) solvent system to provide 56.2 mg (yield of 66%) of 23-O-methylthiomethyl-4'-deoxy mycaminosyl tylonolide. The product showed the following physicochemical properties:

| (i) | NMR (CDCl$_3$) | | |
|---|---|---|---|
| δ(ppm) | H no. | Form | |
| 1.85 | 3 | s | 12-CH$_3$(H$_{22}$) |
| 2.15 | 3 | s | 23-O—CH$_2$—S—CH$_3$ |
| 2.30 | 6 | s | —N(CH$_3$)$_2$ |
| 4.66 | 2 | s | 23-O—CH$_2$—S—CH$_3$ |
| 9.83 | 1 | s | /—CHO(H$_{20}$) |

| (ii) | Colorless amorphous solid (acetone and n-hexane) | | | |
|---|---|---|---|---|
| (iii) | Anal. for C$_{33}$H$_{55}$HO$_9$S: | | | |
| | C (%) | H (%) | N (%) | S (%) |
| Calculated | 61.75 | 8.64 | 2.18 | 4.99 |
| Found | 61.63 | 8.45 | 2.13 | 4.71 |

| (iv) | [α]$_D^{21}$: | −8° (c 1.0, CHCl$_3$) |
|---|---|---|
| (v) | UV | $\lambda_{max}^{MeOH}$: 283 nm (ε = 22,000) |
| (vi) | Rf | 0.37 Wakogel B-5 chloroform-methanol (10:1) |

EXAMPLE 21

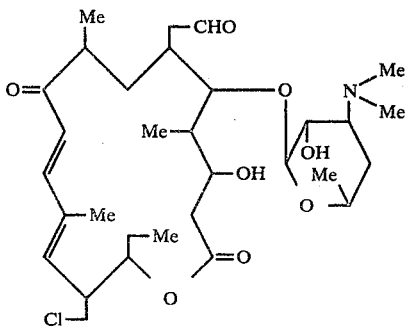

(a). After dissolving 95.8 mg of 4'-deoxy mycaminosyl tylonolide diethyl acetal in 4.8 ml of anhydrous pyridine, 84.5 mg of triphenylphosphine was added to the solution and after ice-cooling the mixture and slowly adding dropwise 24.8 mg of carbon tetrachloride to the mixture with stirring, the reaction was performed for 18 hours at room temperature. Then, after adding 1.0 ml of methanol, the reaction mixture was concentrated, pyridine was azeotropically distilled well with toluene, the residue was dissolved in chloroform, the solution was washed with a saturated aqueous sodium hydrogencarbonate solution, an aqueous 0.1 M sodium thiosulfate solution, and then water, dried by anhydrous sodium sulfate, and concentrated under reduced pressure.

Then, the residue was applied to a column of 10 g of silica gel and after eluting with 20 ml of a chloroform-methanol (50:1) solvent system, the solvent system was changed to a chloroform-methanol (9:1) solvent system to provide 97.6 mg (yield of 99%) of 23-chloro-23,4'-dideoxy mycaminosyl tylonolide diethyl acetal.

By recrystallizing 53.3 mg of the product from a mixture of acetone and n-hexane, 34.5 mg (recrystallization yield of 65%) of the plate crystals thereof were obtained.

(b). After dissolving 61.5 mg of the product obtained in above step (a) in 1.23 ml of acetonitrile, 1.8 ml of an aqueous 0.1 N hydrochloric acid solution was added and the reaction was performed for 60 minutes. Then, after adding 23 mg of sodium hydrogencarbonate to the reaction mixture, the product was extracted with chloroform and the extract was washed with a saturated aqueous sodium sulfate solution, dried by anhydrous sodium sulfate, and concentrated under reduced pressure. The residue was subjected to chromatography by a column of 6 g of silica gel using a chloroform-methanol (7:1) solvent system to provide 28.5 mg of the desired compound, 23-chloro-23,4'-dideoxy mycaminosyl tylonolide. Furthermore, other fractions containing the desired compound were subjected to chromatography by a column of 4 g of silica gel using a chloroform-methanol-concentrated aqueous ammonium (15:1:0.1) solvent system to provide 16.9 mg of the desired compound. The total amount of the product was 45.4 mg (yield of 83%).

The product showed the following physicochemical properties:

| (i) | NMR (CDCl$_3$) | | | |
|---|---|---|---|---|
| δ (ppm) | H no. | Form | J (Hz) | |
| ~1.7 | ~2 | m | | H'$_4$ |
| 2.30 | 6 | s | | 3'-N(CH$_3$)$_2$ |
| 4.22 | 1 | d$_{1',2'}$ | 7.5 | H'$_1$ |
| 5.02 | 1 | m | | H$_{15}$ |
| 5.90 | 1 | d$_{13,14}$ | 10.0 | H$_{13}$ |
| 6.37 | 1 | d$_{10,11}$ | 16.0 | H$_{10}$ |
| 7.43 | 1 | d$_{11,10}$ | 16.0 | H$_{11}$ |

| (ii) | Colorless amorphous solid | | | |
|---|---|---|---|---|
| | (re-precipitated from acetone and n-hexane) | | | |
| (iii) | Anal. for C$_{31}$H$_{50}$NO$_8$Cl: | | | |
| | C (%) | H (%) | N (%) | Cl (%) |
| Calculated | 62.04 | 8.40 | 2.33 | 5.91 |
| Found | 62.22 | 8.47 | 2.10 | 5.82 |

| (iv) | [α]$_D^{23}$: | −8° (c 1.0, CHCl$_3$) |
|---|---|---|
| (v) | UV | $\lambda_{max}^{MeOH}$: 280 nm (ε = 21,000) |
| (vi) | Rf | 0.36 Wakogel B-5 chloroform-methanol (7:1) |

In addition, 4'-deoxy mycaminosyl tylonolide used as the starting material in Example 21 was prepared by the processes of following Reference examples 6 and 7.

REFERENCE EXAMPLE 6

After dissolving 124 mg of 4'-deoxy mycaminosyl tylonolide in 1.24 ml of anhydrous ethanol, 55 mg of anhydrous p-toluenesulfonic acid was added to the solution and the reaction was performed for 30 minutes at room temperature. Then, after neutralizing the reaction mixture with 0.05 ml of triethylene, the mixture was concentrated under reduced pressure. The residue was dissolved in chloroform and the solution was washed with a saturated aqueous sodium hydrogencarbonate and then water, dried by anhydrous sodium sulfate, and concentrated under reduced pressure.

Then, the residue obtained was applied to a column of 12 g of silica gel using first a chloroform-methanol-concentrated aqueous ammonia (30:1:0.1) solvent system and then the solvent system was changed to a chloroform-methanol-concentrated aqueous ammonia (15:1:0.1) solvent system, thereby 128 mg (yield of 92%) of 4'-deoxy mycaminosyl tylonolide diethyl acetal was obtained.

The product showed the following physicochemical properties:

(i) NMR (CDCl₃)

| δ (ppm) | H no. | Form | |
|---|---|---|---|
| ~1.7 | ~2 | m | H'₄ |
| 1.83 | 3 | s | 12-CH₃ |
| 2.32 | 6 | s | —N(CH₃)₂ |
| 3.52 | ~4 | m | ⌈—CH(OCH₂CH₃)₂ |
| 4.73 | 1 | m | ⌈—CH(OEt)₂ |

(ii) Colorless amorphous solid (acetone and n-hexane)
(iii) m.p. 176–179° C. (fine melting point measurement device, made by Yanagimoto Seisakusho, correction was not made)
(iv) Anal. for $C_{35}H_{61}NO_{10}$:

| | C (%) | H (%) | N (%) |
|---|---|---|---|
| Calculated | 64.10 | 9.38 | 2.14 |
| Found | 64.20 | 9.17 | 2.17 |

(v) $[d]_D^{23}$: +8° (c 1.0, CHCl₃)
(vi) UV $\lambda_{max}^{MeOH}$: 282.5 nm (ε = 22,000)
(vii) Rf 0.40 Wakogel B-5 chloroform-methanol (9:1)

REFERENCE EXAMPLE 7

In 7.3 ml of anhydrous ethanol was dissolved 182 mg of 3,23-di-O-tetrahydrofuranyl-4'-deoxy mycaminosyl tylonolide diethyl acetal and after adding thereto 69 mg of pyridinium p-toluenesulfonate, the reaction was performed for 3 hours at 78° C. After allowing to cool the temperature of the reaction mixture to room temperature, the reaction mixture was neutralized with 0.05 ml of triethylamine and concentrated under reduced pressure.

Then, 135 mg of the crude product was subjected to a chromatography by a silica gel column using a chloroform-methanol-concentrated aqueous ammonia (15:1:0.1) solvent system and the product obtained was crystallized from a mixture of acetone and n-hexane to provide 89.1 mg of 4'-deoxy mycaminosyl tylonolide diethyl acetal as the primary crystal.

The product had the same physicochemical properties as those of the product obtained in Reference example 6.

EXAMPLE 22

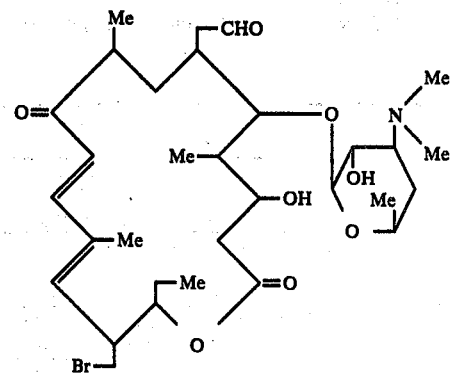

By following the same procedure as in Example 21 using 131.6 mg of 4'-deoxy mycaminosyl tylonolide diethyl acetal and 67.4 mg of carbon tetrabromide, 45.7 mg (yield of 86%) of 23-bromo-23,4'-dideoxy mycaminosyl tylonolide was obtained.

The product showed the following physicochemical properties:

(i) NMR (CDCl₃)

| δ(ppm) | H no. | Form | J (Hz) | |
|---|---|---|---|---|
| ~1.7 | ~2 | m | | H'₄ |
| 1.83 | 3 | s | | 3'-N(CH₃)₂ |
| 2.30 | 6 | s | 7.5 | H'₂ |
| 4.22 | 1 | d₁',₂' | 7.5 | H'₁ |
| 4.99 | 1 | m | | H₁₅ |
| 5.87 | 1 | d₁₃,₁₄ | 10.0 | H₁₃ |
| 6.36 | 1 | d₁₀,₁₁ | 16.0 | H₁₆ |
| 7.43 | 1 | d₁₁,₁₀ | 16.0 | H₁₁ |
| 9.80 | 1 | like s | | H₂₀ |

(ii) Colorless amorphous solid (acetone and n-hexane)
(iii) Anal. for $C_{31}H_{50}NO_8Br$:

| | C (%) | H (%) | N (%) | Cl (%) |
|---|---|---|---|---|
| Calculated | 57.76 | 7.82 | 2.17 | 12.40 |
| Found | 57.83 | 7.80 | 2.00 | 12.3 |

(iv) $[\alpha]_D^{23}$: +11° (c 1.0, CHCl₃)

(v) UV $\lambda_D^{MeOH}$: 280 nm (ε = 21,000)

(vi) Rf 0.36 Wakogel B - 5 chloroform-methanol (7:1)

EXAMPLE 23

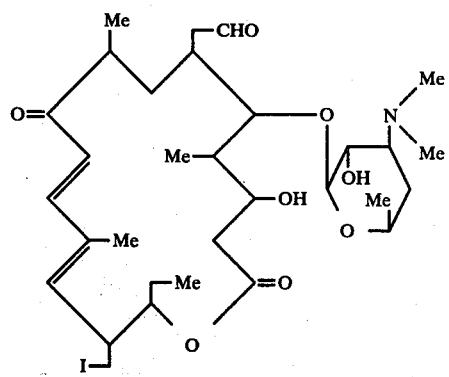

By following the same procedure as in Example 22 using 111.6 mg of 4'-deoxy mycaminosyl tylonolide diethyl acetal and 106 mg of carbon tetraiodide, 43.4 mg (yield of 81%) of 23,4'-dideoxy-23-iodo mycaminosyl tylonolide was obtained.

The product showed the following physicochemical properties:

(i) NMR (CDCl$_3$)

| δ(ppm) | H no. | Form | |
|---|---|---|---|
| ~1.7 | ~2 | m | H'$_4$ |
| 1.83 | 3 | s | H$_{22}$ |
| 2.30 | 6 | s | 3'-N(CH$_3$)$_2$ |

(ii) Colorless amorphous solid (acetone and n-hexane)
(iii) Anal. for C$_{31}$H$_{50}$NO$_8$I

| | C (%) | H (%) | N (%) | I (%) |
|---|---|---|---|---|
| Calculated | 53.83 | 7.29 | 2.03 | 18.35 |
| Found | 53.65 | 7.41 | 1.90 | 18.5 |

(iv) $[α]_D^{23}$: +56° (c 1.0, CHCl$_3$)

(v) UV $λ_{max}^{MeOH}$: 281 nm (ε = 24,000)

(vi) Rf 0.36 Wakogel B - 5 chloroform-methanol (7:1)

EXAMPLE 24

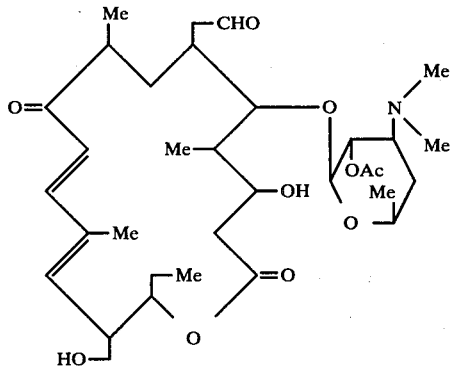

In 0.75 ml of anhydrous acetonitrile was dissolved 149 mg of 4'-deoxy mycaminosyl tylonolide and after adding thereto 39.2 mg of acetic anhydride, the reaction was performed for 60 minutes. The reaction mixture was concentrated under reduced pressure, the residue was dissolved in chloroform, and the solution was washed once each with a saturated aqueous sodium hydrogencarbonate solution, a saturated aqueous sodium sulfate solution, and then water, dried by anhydrous sodium sulfate, and concentrated under reduced pressure to provide 150.3 mg (yield of 94%) of 2'-O-acetyl-4'-deoxy mycaminosyl tylonolide.

The product showed the following physicochemical properties:

(i) NMR (CDCl$_3$)

| δ(ppm) | H no. | Form | Reversion |
|---|---|---|---|
| ~1.7 | ~2 | m | H'$_4$ |
| 1.85 | 3 | s | H$_{22}$(12-CH$_3$) |
| 2.09 | 3 | s | 2'-O—COCH$_3$ |
| 2.28 | 6 | s | 3'-N(CH$_3$)$_2$ |

(ii) Colorless amorphous solid (acetone and n-hexane)
(iii) Anal. for C$_{33}$H$_{53}$NO$_{10}$:

| | C (%) | H (%) | N (%) |
|---|---|---|---|
| Calculated | 63.54 | 8.56 | 2.25 |
| Found | 63.71 | 8.58 | 2.16 |

(iv) $[α]_D^{20}$: +2° (c 1.0, CHCl$_3$)

(v) UV $λ_{max}^{EtOH}$: 283 nm (ε = 25,000)

(vi) Rf 0.40 Wakogel B-5 benzene-acetone (3:3)

EXAMPLE 25

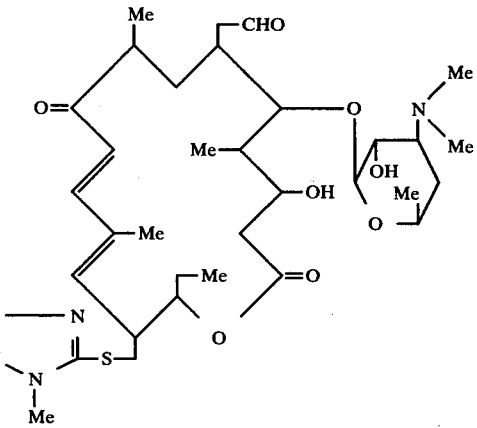

After dissolving 80.0 mg of 23-deoxy-23-iodo-4'-deoxy mycaminosyl tylonolide diethyl acetal and 26 mg of 1-methyl-1H-tetrazol-5-ylthiol in anhydrous acetonitrile, 8.8 mg of sodium hydride (57% mineral oil) was added to the solution and the reaction was performed overnight at 18° C. The reaction mixture was concentrated under reduced pressure, and residue was dissolved in 4 ml of chloroform, and the solution was washed with a saturated aqueous sodium hydrogencarbonate solution and a saturated aqueous sodium sulfate solution, and then concentrated under reduced pressure.

Then, the residue was dissolved in 1.6 ml of acetonitrile and after adding thereto 2.1 ml of an aqueous 0.1 N hydrochloric acid solution, the reaction was performed for 60 minutes at 18° C. After adding 26.5 mg of sodium hydrogencarbonate to the reaction mixture, the product was extracted with 1.5 ml of chloroform and the extract was washed with a saturated aqueous sodium sulfate solution, dried by anhydrous sodium sulfate, and concentrated under reduced pressure.

The residue obtained was purified by a silica gel column using a chloroform-methanol (7:1) solvent system and then recrystallized from a mixture of chloroform and n-hexane to provide 53.5 mg (yield of 75%) of 23,4'-dideoxy-23-(1-methyl-1H-tetrazol-5-ylthio) mycaminosyl tylonolide as the primary crystal.

The product showed the following physicochemical properties:

(i) NMR (CDCl$_3$)

| δ(ppm) | H no. | Form | |
|---|---|---|---|
| 2.30 | 6 | s | 3'-NMe$_2$ |
| 3.92 | 3 | s | 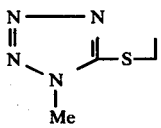 |

-continued

| 9.83 | 1 | s | | H20 |
|------|---|---|---|-----|

(ii) Anal. for C₃₃H₅₃N₅O₈S:

| | C (%) | H (%) | N (%) | S (%) |
|---|---|---|---|---|
| Calculated | 58.30 | 7.86 | 10.30 | 4.72 |
| Found | 58.41 | 7.80 | 10.56 | 4.83 |

(iii) $[\alpha]_D^{22}$: +135° (c 1.0, CHCl₃)
(iv) m.p. 236–238° C. (meltd.)
(v) Colorless columnar crystal (chloroform and n-hexane)

In addition, the raw material used in this example was prepared by the process shown in the following reference example.

REFERENCE EXAMPLE 8

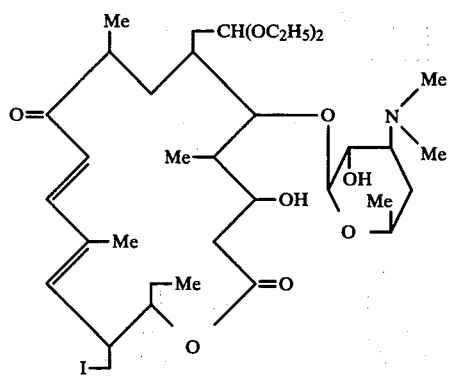

After dissolving 111.6 mg of 4'-deoxy mycaminosyl tylonolide diethyl acetal in 5.6 ml of anhydrous pyridine, 89.2 mg of triphenylphosphine was added and, after further adding thereto 88.3 mg of carbon tetraiodide with stirring under ice-cooling, the reaction was performed for one hour at the same temperature. Then, after adding 1.1 ml of methanol to the reaction mixture, the mixture was concentrated under reduced pressure. After performing azeotropic distillation of pyridine with toluene, 5.6 ml of chloroform was added to the residue to form precipitates. The precipitates were filtered by a cotton filter and after washing the precipitates with a small amount of chloroform, the chloroform layers were combined with each other. The chloroform solution was washed once with a saturated aqueous sodium hydrogencarbonate solution and an aqueous 0.1 M sodium thiosulfate solution, dried by anhydrous sodium sulfate, and concentrated under reduced pressure.

The residue formed was applied to a column of 12 g of silica gel and after eluting with a chloroform-methanol (50:1) solvent system, the product was developed by a chloroform-methanol (10:1) solvent system to provide 112.5 mg (yield of 87%) of 23,4'-dideoxy-23-iodo mycaminosyl tylonolide diethyl acetal.

The product showed the following physicochemical properties:

| (i) sNMR (CDCl₃) | | | | |
|---|---|---|---|---|
| δ (ppm) | H no. | Form | J (Hz) | |
| ~1.7 | ~2 | m | | H'₄ |
| 2.31 | 6 | s | | 3'-N(CH₃)₂ |
| ~3.5 | ~4 | m | | CHCOCH₂CH₃ |

-continued

| 4.28 | 1 | $d_{1',2'}$ | 7.5 | H'₁ |
|------|---|---|------|-----|
| 5.70 | 1 | $d_{13,14}$ | 10.0 | H₁₃ |
| 6.38 | 1 | $d_{10,11}$ | 16.5 | H₁₀ |
| 7.32 | 1 | $d_{11,10}$ | 16.5 | H₁₁ |

(ii) Colorless amorphous solid (acetone and n-hexane)
(iii) Anal. for C₃₅H₆₀HO₉I:

| | C (%) | H (%) | N (%) | I (%) |
|---|---|---|---|---|
| Calculated | 54.90 | 7.90 | 1.83 | 16.57 |
| Found | 54.88 | 7.75 | 1.77 | 16.28 |

(iv) $[\alpha]_D^{23}$: +78° (c 1.0, CHCl₃)
(v) UV $\lambda_{max}^{MeOH}$: 281 nm (ε = 24,000)
(vi) Rf 0.39 Wakogel B-5 chloroform-methanol (10:1)

EXAMPLE 26

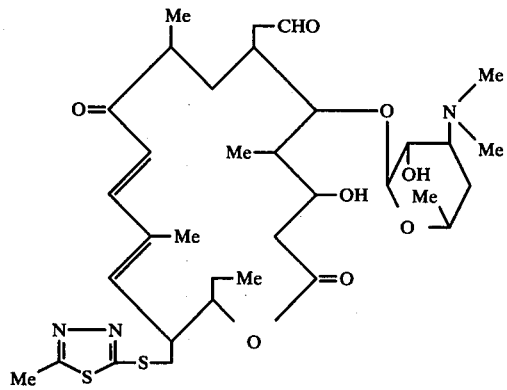

After dissolving 101.6 mg of 23,4'-dideoxy-23-iodo mycaminosyl tylonolide diethyl acetal and 35.1 mg of 2-methyl-1,3,4-thiadiazol-5-ylthiol in 2.0 ml of anhydrous acetonitrile, 11.2 mg of sodium hydride was added to the solution and the reaction was performed overnight at 18° C. The reaction mixture was concentrated under reduced pressure, the residue was dissolved in chloroform, and the solution was washed with a saturated aqueous sodium hydrogencarbonate solution and a saturated aqueous sodium sulfate solution, and concentrated under reduced pressure.

The residue was dissolved in 2 ml of acetonitrile and after adding thereto 2.7 ml of an aqueous 0.1 N hydrochloric acid solution, the reaction was performed for 60 minutes. After adding 33.5 mg of sodium hydrogencarbonate to the reaction mixture, the product was extracted with chloroform and the extract was washed with a saturated aqueous sodium sulfate solution, dried by anhydrous sodium sulfate, and concentrated under reduced pressure.

The residue obtained was subjected to a chromatography by a silica gel column using a chloroform-methanol (7:1) solvent system to provide 87.3 mg (yield of 94%) of 23,4'-dideoxy-23-(2-methyl-1,3,4-thidiazol-5-ylthio) mycaminosyl tylonolide.

The product showed the following physicochemical properties:

| (i) NMR (CDCl₃) | | | |
|---|---|---|---|
| δ (ppm) | H no. | Form | |
| 2.31 | 6 | s | 3'-NCH₃ |

-continued

| | | | |
|---|---|---|---|
| 2.76 | s | s | N═══N, Me─⫨S, S⫩─ |
| 9.83 | 1 | s | H₂O |

(ii) Anal. for $C_{34}H_{53}N_3O_8S_2$:

| | C (%) | H (%) | N (%) | S (%) |
|---|---|---|---|---|
| Calculated | 58.64 | 7.68 | 6.04 | 9.21 |
| Found | 58.41 | 7.80 | 6.24 | 9.32 |

(iii) $[\alpha]_D^{22}$: +170° (c 1.0, CHCl₃)

EXAMPLE 27

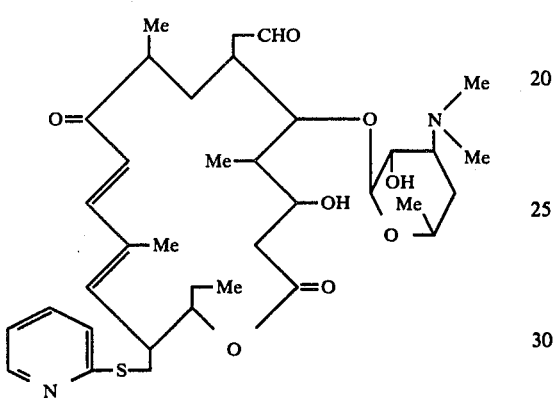

After dissolving 70.0 mg of 23,4'-dideoxy-23-iodo mycaminosyl tylonolide and 20.3 mg of 2-mercaptopyridine in 1.4 ml of anhydrous acetonitrile, 7.7 mg of sodium hydride (57% mineral oil) was added to the solution and the reaction was performed for 60 minutes.

The reaction mixture obtained was concentrated under reduced pressure, the residue was dissolved in chloroform, and the solution was washed with a saturated aqueous sodium hydrogencarbonate solution and then a saturated sodium sulfate solution, dried by anhydrous sodium sulfate, and concentrated under reduced pressure.

After dissolving the residue in 1.4 ml of acetonitrile, 2.3 ml of a 0.1 N hydrochloric acid solution was added to the solution and the reaction was performed for 60 minutes. Then, after adding 27 mg of sodium hydrogencarbonate to the reaction mixture, the product was extracted with chloroform and the extract was washed with a saturated aqueous sodium sulfate solution, dried by anhydrous sodium sulfate, and concentrated under reduced pressure.

The residue obtained was subjected to chromatography by a silica gel column using a chloroform-methanol (7:1) solvent system to provide 55.0 mg (yield of 94%) of 23,4'-dideoxy-23-(pyridine-2-ylthio) mycaminosyl tylonolide.

The product showed the following physicochemical properties:

(i) NMR (CDCl₃)

| (ppm) | H no. | Form | |
|---|---|---|---|
| 2.31 | 6 | s | 3'-NMe₂ |

| 6.98–7.65 | 3 | m | (pyridine H) |
| 8.50 | 1 | m | (pyridine H) |
| 9.83 | 1 | s | H₂O |

(ii) Anal. for $C_{36}H_{54}N_2O_8S$:

| | C (%) | H (%) | N (%) | S (%) |
|---|---|---|---|---|
| Calculated | 64.07 | 8.07 | 4.15 | 4.75 |
| Found | 64.88 | 8.03 | 3.95 | 4.47 |

(iii) $[\alpha]_D^{22}$: +131° (c 1.0, CHCl₃)

EXAMPLE 28

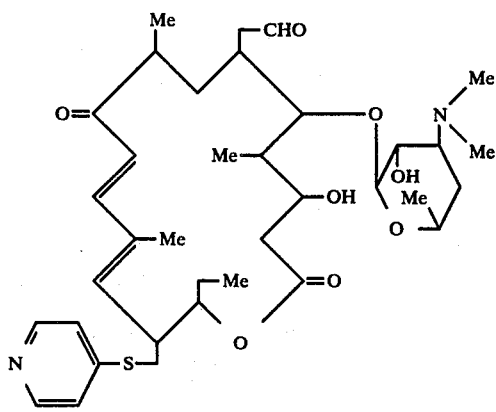

After dissolving 73.2 mg of 23,4'-dideoxy-23-iodo mycaminosyl tylonolide diethyl acetal and 21.2 mg of 4-mercaptopyridine in 1.4 ml of anhydrous acetonitrile, 8.6 mg of sodium hydride (57% mineral oil) was added to the solution and the reaction was performed for 20 minutes. The reaction mixture was concentrated, the residue was dissolved in chloroform, and the solution was washed with a saturated aqueous sodium hydrogencarbonate solution and then a saturated aqueous sodium sulfate solution, dried by anhydrous sodium sulfate, and concentrated under reduced pressure.

The residue obtained was dissolved in 1.4 ml of acetonitrile and after adding thereto 2.4 ml of a 0.1 N hydrochloric acid solution, the reaction was performed for 60 minutes. After adding 32 mg of sodium hydrogencarbonate to the reaction mixture, the product was extracted with chloroform, and the extract was washed with a saturated aqueous sodium sulfate solution, dried by anhydrous sodium sulfate, and concentrated under reduced pressure.

The residue obtained was subjected to chromatography by a silica gel column using a chloroform-methanol (7:1) solvent system to provide 59.4 mg (yield of 95%) of 23,4'-dideoxy-23-(pyridine-4-ylthio) mycaminosyl tylonolide.

When 40 mg of the product was recrystallized from a mixture of acetone and n-hexane, 32.2 mg (yield of 81%) of the pure crystals thereof were obtained.

The product showed the following physicochemical properties:

| (i) NMR (CDCl₃) | | | | |
|---|---|---|---|---|
| δ (ppm) | H no. | Form | J(Hz) | |
| 2.31 | 6 | s | | 3'NMe₂ |
| 3.24 | 1 | dd 2',1' / 2',3' | 7.5 / 10.0 | H'₂ |
| 7.17 | s | m | | (pyridyl-S) |
| 8.50 | 2 | m | | (pyridyl-S) |
| 9.83 | 1 | s | | H₂₀ |

(ii) Anal. for $C_{36}H_{54}N_2O_8S$:

| | C (%) | H (%) | N (%) | S (%) |
|---|---|---|---|---|
| Calculated | 64.07 | 8.07 | 4.15 | 4.75 |
| Found | 64.27 | 8.10 | 3.96 | 4.59 |

(iii) $[\alpha]_D^{22} + 108°$ (c 1.0, CHCl₃)
(iv) m.p. 171–173° C. (melted)
(v) Colorless prism crystal and n-hexane

EXAMPLE 29

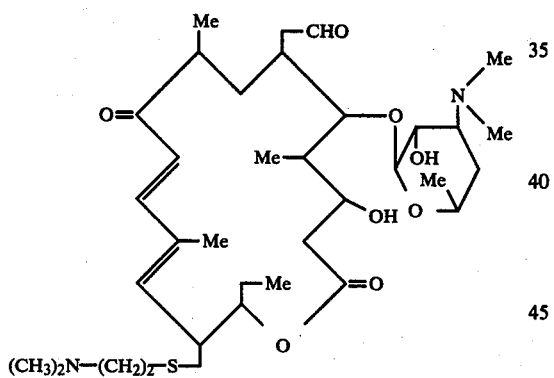

After dissolving 59.4 mg of 23,4'-dideoxy-23-iodo mycaminosyl tylonolide diethyl acetal and 22.0 mg of 2-dimethylaminoethanethiol hydrochloride in anhydrous acetonitrile, 13 mg of sodium hydride (57% mineral oil) was added to the solution with stirring under ice-cooling and after allowing to raise the temperature to room temperature (18° C.) after 5 minutes, the reaction was performed for 30 minutes at 50° C. The reaction mixture was concentrated, the residue was dissolved in chloroform, and the solution was washed with a saturated aqueous sodium hydrogencarbonate solution and then a saturated sodium sulfate solution, dried by anhydrous sodium sulfate, and concentrated under reduced pressure.

The residue obtained was dissolved in 1.2 ml of acetonitrile and after adding thereto 3.1 ml of an aqueous hydrochloric acid solution, the reaction was performed for 60 minutes.

After adding 33 mg of sodium hydrogencarbonate and then 1 ml of a saturated sodium hydrogencarbonate solution to the reaction mixture, the product was extracted with chloroform and the extract was washed with a saturated aqueous sodium sulfate solution, dried by anhydrous sodium sulfate, and concentrated under reduced pressure.

The residue obtained was subjected to chromatography by a silica gel column using a chloroform-methanol-concentrated aqueous ammonia (12:1:0.1) solvent system to provide 35.8 mg (yield of 69%) of 23,4'-dideoxy-23-(2-dimethylaminoethanethio) mycaminosyl tylonolide.

The product showed the following physicochemical properties:

| (i) NMR (CDCl₃) | | | |
|---|---|---|---|
| δ (ppm) | H no. | Form | |
| 2.27 | 6 | s | 23-(CH₂)₂NMe₂ |
| 2.30 | 6 | s | 3'-NMe₂ |
| 9.82 | 1 | s | H₂₀ |

(ii) Anal. for $C_{35}H_{60}N_2O_8S$:

| | C (%) | H (%) | N (%) | S (%) |
|---|---|---|---|---|
| Calculated | 62.84 | 9.04 | 4.19 | 4.79 |
| Found | 62.58 | 9.01 | 4.03 | 4.62 |

(iii) $[\alpha]_D^{22} + 76°$ (c 0.5, CHCl₃)

What is claimed is:

1. A compound derived from tylosin having the formula

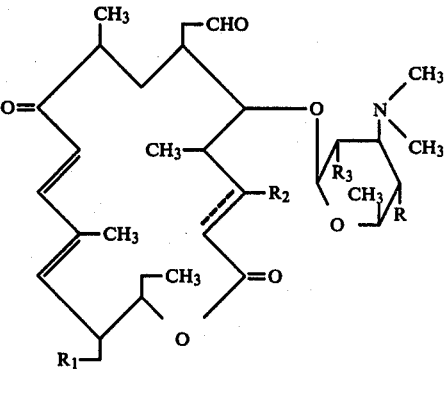

wherein R represents a hydrogen atom or a hydroxyl group; $R_1$ represents a halogen atom, a hydroxyl group, a tetrahydrofuranyloxy group, a tetrahydropyranyloxy group, a tetrahydrothiofuranyloxy group, a tetrahydrothiopyranyloxy group, an alkanoyloxy group, an arylcarbonyloxy group, an aralkylcarbonyloxy group, a lower alkylthiomethyloxy group, a substituted or unsubstituted heterocyclic thio group, a mono- or di-lower alkylamino lower alkylthio group, or a group of the formula

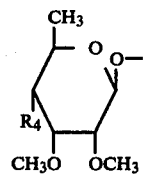

wherein $R_4$ represents a hydroxyl group or an alkanoyloxy group; $R_2$ represents a hydrogen atom, a hydroxyl group, or an alkanoyloxy group; $R_3$ represents a hydroxyl group or an alkanoyloxy group; and represents a single bond or a double bond but, when $R_2$ is a hydrogen atom, represents a double bond.

2. The tylosin derivative as claimed in claim 1 wherein $R_2$ and $R_3$ are a hydroxyl group.

3. The tylosin derivative of claim 1 which is 4'-deoxy mycaminosyl tylonolide.

4. The tylosin derivative of claim 1 which is 23-O-acetyl-4'-deoxy mycaminosyl tylonolide.

5. The tylosin derivative of claim 1 which is 23-O-propionyl- 4'-deoxy mycaminosyl tylonolide.

6. The tylosin derivative of claim 1 which is 23-O-tetrahydrothiofuranyl-4'-deoxy mycaminosyl tylonolide.

7. The tylosin derivative of claim 1 which is 23-O-tetrahydrothiopyranyl-4'-deoxy mycaminosyl tylonolide.

8. The tylosin derivative of claim 1 which is 23-O-methylthiomethyl-4'-deoxy mycaminosyl tylonolide.

9. The tylosin derivative of claim 1 which is 23-chloro-23,4'-dideoxy mycaminosyl tylonolide.

10. The tylosin derivative of claim 1 which is 23,4'-dideoxy-23-(pyridyl-4-ylthio) mycaminosyl tylonolide.

11. An antibiotic composition comprising a therapeutically effective amount of a tylosin derivative of claim 1 in combination with a pharmaceutically acceptable carrier.

12. The composition of claim 11 wherein said composition is in the form of a tablet, a capsule, a powder, or a liquid.

13. A method of providing an antibiotic effect comprising administering a therapeutically effective amount of the composition of claim 11 to a warm blooded animal.

14. The method of claim 13 wherein said composition is administered orally or parenterally in a dosage amount varying between about 10 and 1000 mg. 1 to 4 times a day.

15. The tylosin derivative as claimed in claim 1 wherein said heterocyclic thio group is selected from the group consisting of thienylthio group, pyrrolylthio group, pyrrolidinylthio group, pyridylthio group, piperidinylthio group, pyrazinylthio group, thiazolylthio group, thiadiazolylthio group, triazolylthio group, tetrazolylthio group, and morpholinothio group, and, when said heterocyclic thio group is substituted, the substituent is selected from the group consisting of lower alkyl groups and lower alkoxy groups.

* * * * *